United States Patent
Bix

(10) Patent No.: US 11,413,326 B2
(45) Date of Patent: Aug. 16, 2022

(54) COMPOSITIONS AND METHODS FOR ENHANCING NEURO-REPAIR

(71) Applicant: University of Kentucky Research Foundation, Lexington, KY (US)

(72) Inventor: Gregory J. Bix, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 29 days.

(21) Appl. No.: 16/769,750

(22) PCT Filed: Dec. 13, 2018

(86) PCT No.: PCT/US2018/065390
§ 371 (c)(1),
(2) Date: Jun. 4, 2020

(87) PCT Pub. No.: WO2019/118689
PCT Pub. Date: Jun. 20, 2019

(65) Prior Publication Data
US 2020/0384075 A1    Dec. 10, 2020

Related U.S. Application Data

(60) Provisional application No. 62/598,308, filed on Dec. 13, 2017.

(51) Int. Cl.
| | |
|---|---|
| *A61K 38/17* | (2006.01) |
| *A61K 9/00* | (2006.01) |
| *A61P 25/28* | (2006.01) |
| *A61P 25/00* | (2006.01) |
| *C07K 14/47* | (2006.01) |

(52) U.S. Cl.
CPC ........ *A61K 38/1709* (2013.01); *A61K 9/0019* (2013.01); *A61P 25/28* (2018.01)

(58) Field of Classification Search
CPC .. A61K 38/17; A61K 38/1709; A61K 9/0019; A61K 9/00; A61P 25/28; A61P 25/00; C07K 14/47
See application file for complete search history.

(56) References Cited

U.S. PATENT DOCUMENTS

| | | |
|---|---|---|
| 2010/0168025 A1 | 7/2010 | Bix |
| 2012/0003180 A1 | 1/2012 | Bix |

OTHER PUBLICATIONS

Lee, B., et al. Perlecan domain V is neuroprotective and proangiogenic following ischemic stroke in rodents. J Clin Invest 121, 3005-3023 (2011).
Al-Ahmad, A.J., Lee, B., Saini, M. & Bix, G.J. Perlecan domain V modulates astrogliosis in vitro and after focal cerebral ischemia through multiple receptors and increased nerve growth factor release. Glia 59, 1822-1840 (2011).
Bix, G., Gowling, E. & Clarkson, A. Perlecan domain V is neuroprotective and affords functional improvement in a photothromotic stroke model in young and aged mice. Transl Stroke Res 4, 515-523 (2013).
Roberts, J., Kahle, M.P. & Bix, G.J. Perlecan and the blood-brain barrier: beneficial proteolysis? Frontiers in pharmacology 3, 155 (2012).
Roediger, M., Kruegel, J., Miosge, N. & Gersdorff, N. Tissue distribution of perlecan domains III and V during embryonic and fetal human development. Histology and histopathology 24, 859-868 (2009).
Gustafsson, E., Almonte-Becerril, M., Bloch, W. & Costell, M. Perlecan maintains microvessel integrity in vivo and modulates their formation in vitro. PLoS One 8, e53715 (2013).
Soulintzi, N. & Zagris, N. Spatial and temporal expression of perlecan in the early chick embryo. Cells, tissues, organs 186, 243-256 (2007).
Giros, A., Morante, J., Gil-Sanz, C., Fairen, A. & Costell, M. Perlecan controls neurogenesis in the developing telencephalon. BMC Dev Biol 7, 29 (2007).
Kerever, A., et al. Perlecan is required for FGF-2 signaling in the neural stem cell niche. Stem cell research 12, 492-505 (2014).
Nakamura, R., Nakamura, F. & Fukunaga, S. Diverse functions of perlecan in central nervous system cells in vitro. Animal Science Journal 86, 904-911 (2015).
Arvidsson, A., Collin, T., Kirik, D., Kokaia, Z. & Lindvail, O. Neuronal replacement from endogenous precursors in the adult brain after stroke. Nat Med 8, 963-970 (2002).
Lichtenwalner, R. & Parent, J. Adult neurogenesis and the ischemic forebrain. J Cereb Blood Flow Metab 26, 1-20 (2006).
Massouh, M. & Saghatelyan, A. De-routing neuronal precursors in the adult brain to sites of injury: role of the vasculature. Neuropharmacology 58, 877-883 (2010).
Thored, P., et al. Long-term neuroblast migration along blood vessels in an area with transient angiogenesis and increased vascularization after stroke. Stroke; a journal of cerebral circulation 38, 3032-3039 (2007).
Wang, Y., et al. VEGF-overexpressing transgenic mice show enhanced post-ischemic neurogenesis and neuromigration. Journal of neuroscience research 85, 740-747 (2007).
Ohab, J.J. & Carmichael, S.T. Poststroke neurogenesis: emerging principles of migration and localization of immature neurons. The Neuroscientist: a review journal bringing neurobiology, neurology and psychiatry 14, 369-380 (2008).
Fukuda, S., et al. Focal cerebral ischemia induces active proteases that degrade microvascular matrix. Stroke; a journal of cerebral circulation 35, 998-1004 (2004).
Kahle, M.P. & Bix, G.J. Neuronal restoration following ischemic stroke: influences, barriers, and therapeutic potential. Neurorehabilitation and neural repair 27, 469-478 (2013).
Parham, C., et al. Perlecan Domain V Inhibits Amyloid-B Activation of the a2b1 Integrin-Mediated Neurotoxic Signaling Cascade. J Alzheimers Disease 54, 1629-1647 (2016).

(Continued)

*Primary Examiner* — Julie Ha
(74) *Attorney, Agent, or Firm* — Stites & Harbison PLLC; Mandy Wilson Decker; Gary N. Stewart

(57) ABSTRACT

Methods for enhancing recovery after an ischemic injury, including cerebral ischemia and stroke, by administration of therapeutic amounts of Domain V protein are described.

9 Claims, 20 Drawing Sheets

(56) References Cited

OTHER PUBLICATIONS

Wright, S., et al. Perlecan domain V inhibits a2 integrin-mediated amyloid-B neurotoxicity. Neurobiology of aging 33, 1379-1388 (2010).
Tisay, K.T. & Key, B. The extracellular matrix modulates olfactory neurite outgrowth on ensheathing cells. The Journal of Neuroscience: the official journal of the Society for Neuroscience 19, 9890-9899 (1999).
Gupton, S.L. & Gertler, F.B. Integrin signaling switches the cytoskeletal and exocytic machinery that drives neuritogenesis. Developmental cell 18, 725-736 (2010).
Bradshaw, A.D., et al. Integrin alpha 2 beta 1 mediates interactions between developing embryonic retinal cells and collagen. Development 121, 3593-3602 (1995).
Leone, D.P., et al. Regulation of neural progenitor proliferation and survival by beta1 integrins. Journal of cell science 118, 2589-2599 (2005).
Kouroupi, G., et al. Lentivirus-mediated expression of insulin-like growth factor-I promotes neural stem/precursor cell proliferation and enhances their potential to generate neurons. Journal of neurochemistry 115, 460-474 (2010).
Anderson, M.F., Aberg, M.A., Nilsson, M. & Eriksson, P.S. Insulin-like growth factor-I and neurogenesis in the adult mammalian brain. Brain research. Developmental brain research 134, 115-122 (2002).
Overman, J.J., et al. A role for ephrin-A5 in axonal sprouting, recovery, and activity-dependent plasticity after stroke. Proceedings of the National Academy of Sciences of the United States of America 109, E2230-2239 (2012).
Clarke, D.N., et al. Perlecan Domain V induces VEGf secretion in brain endothelial cells through integrin alpha5beta1 and ERK-dependent signaling pathways PLoS One 7, e45257 (2012).
Gao, P., et al. Attenuation of brain response to vascular endothelial growth factor-mediated angiogenesis and neurogenesis in aged mice. Stroke; a journal of cerebral circulation 40, 3596-3600 (2009).
Murphy, T.H. & Corbett, D. Plasticity during stroke recovery: from synapse to behaviour. Nature reviews. Neuroscience 10, 861-872 (2009).
Biernaskie, J., Chernenko, G. & Corbett, D. Efficacy of rehabilitative experience declines with time after focal ischemic brain injury. The Journal of neuroscience : the official journal of the Society for Neuroscience 24, 1245-1254 (2004).
Clarkson, A.N., Huang, B.S., Macisaac, S.E., Mody, I. & Carmichael, S.T. Reducing excessive GABA-mediated tonic inhibition promotes functional recovery after stroke. Nature 468, 305-309 (2010).
Wahl, A.S., et al. Neuronal repair. Asynchronous therapy restores motor control by rewiring of the rat corticospinal tract after stroke. Science 344, 1250-1255 (2014).
Soleman, S., Yip, P.K., Duricki, D.A. & Moon, L.D. Delayed treatment with chondroitinase ABC promotes sensorimotor recovery and plasticity after stroke in aged rats. Brain : a journal of neurology 135, 1210-1223 (2012).
Chollet, F., et al. Fluoxetine for motor recovery after acute ischaemic stroke (FLAME): a randomised placebo-controlled trial. The Lancet. Neurology 10, 123-130 (2011).
Clarkson, A.N., Parker, K., Nilsson, M., Walker, F.R. & Gowing, E.K. Combined ampakine and BDNF treatments enhance poststroke functional recovery in aged mice via AKT-CREB signaling. J Cereb Blood Flow Metab 35, 1272-1279 (2015).
Sun, X., et al. Fluoxetine enhanced neurogenesis is not translated to functional outcome in stroke rats. Neuroscience letters 603, 31-36 (2015).
Guo, Y., et al. Effect of using fluoxetine at different time windows on neurological functional prognosis after ischemic stroke. Restorative neurology and neuroscience 34, 177-187 (2016).
Saini, M.G. & Bix, G.J. Oxygen-glucose deprivation (OGD) and interleukin-1 (IL-1) differentially modulate cathepsin B/L mediated generation of neuroprotective perlecan LG3 by neurons. Brain research 1438, 65-74 (2012).
Ma, F.M., et al. Plasma Matrix Metalloproteinases in Patients with Stroke During Intensive Rehabilitation Therapy. Arch Phys Med Rehabil 97, 1832-1840 (2016).
Kearns, S.M., Laywell, E.D., Kukekov, V.K. & Steindler, D.A. Extracellular matrix effects on neurosphere cell motility. Experimental neurology 182, 240-244 (2003).
Coles, C.H., et al. Proteoglycan-specific molecular switch for RPTPsigma clustering and neuronal extension. Science 332, 484-488 (2011).
Hill, J.J., Jin, K., Mao, X.O., Xie, L. & Greenberg, D.A. Intracerebral chondroitinase ABC and heparan sulfate proteoglycan glypican improve outcome from chronic stroke in rats. Proceedings of the National Academy of Sciences of the United States of America 109, 9155-9160 (2012).
Huat T.J., Khan A.A., Pati S., Mustafa Z., Abdullah J.M., Jaafar H. IGF-1 enhances cell proliferation and survival during early differentiation of mesenchymal stem cells to neural progenitor-like cells. BMC Neurosci 15:91-104 (2014).
Blumbach, K., et al. Dwarfism in mice lacking collagen-binding integrins alpha2beta1 and alpha11beta1 is caused by severely diminished IGF-1 levels. The Journal of biological chemistry 287, 6431-6440 (2012).
Ohab, J.J., et al., A Neurovascular Niche for Neurogenesis after Stroke, Journal of Neuroscience 26(50) 13007-13016 (2006).
Navaratna, S.G., et al., Mechanisms and Targets for angiogenic therapy after stroke, Cell Adhesion & Migration 3(2) 216-223 (2009).
Lo, E..H, A new penumbra: transitioning from injury to repair after stroke, Nature Medicine 4(5) 497-500 (2008).

PBS Vehicle         DV Treated

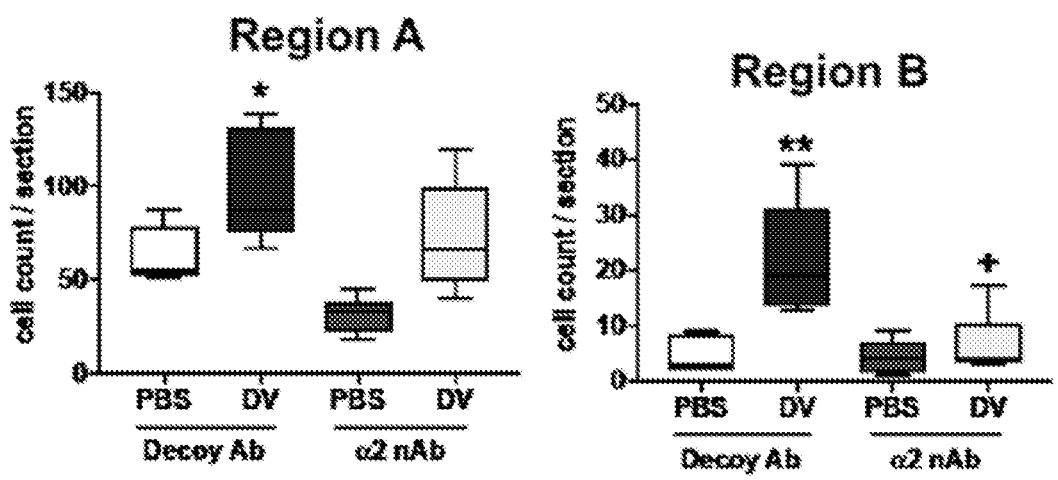
FIG. 8E
FIG. 8F
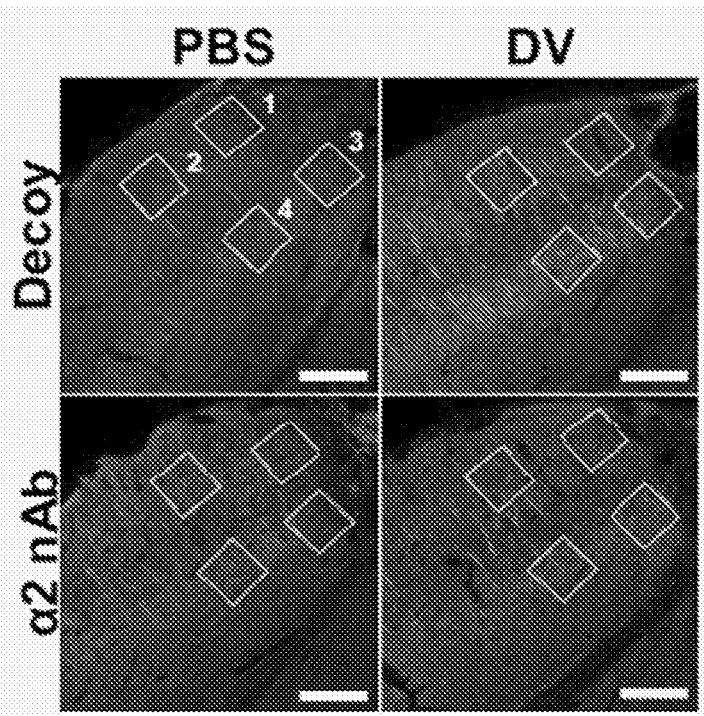
FIG. 8G
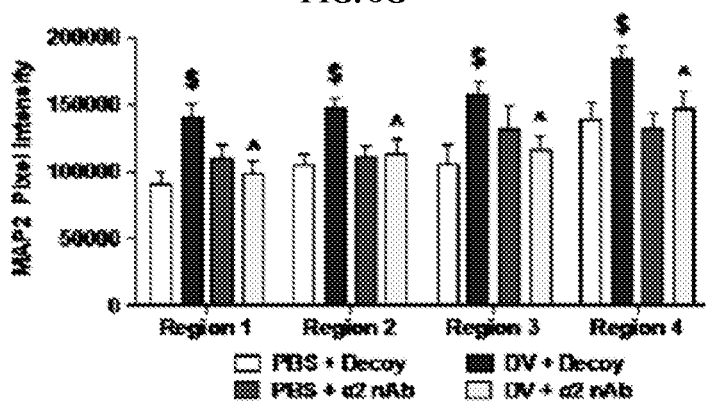
FIG. 8H

COMPOSITIONS AND METHODS FOR ENHANCING NEURO-REPAIR

RELATED APPLICATIONS

This application claims the benefit of U.S. Provisional Application Ser. No. 62/598,308, filed Dec. 13, 2017, the entire disclosure of which is incorporated herein by this reference.

GOVERNMENT INTEREST

This invention was made with government support under Grant No. NIH 1R21NS079960. The government has certain rights in the invention.

TECHNICAL FIELD

The presently-disclosed subject matter relates to the treatment of ischemia, including cerebral ischemia and stroke. In particular, embodiments of the presently-disclosed subject matter relate to methods for preventing and/or treating ischemia and potential infarction that utilize Perlecan Domain V.

BACKGROUND

Tissues deprived of blood and oxygen undergo ischemic necrosis or infarction with possible irreversible organ damage. Stroke is a leading cause of death and disability, with ~15 million new cases worldwide annually. Ischemic stroke, defined as the blockade of a blood vessel supplying the brain (by a blood clot), comprises ~80% of all strokes, while the remaining 20% are the result of blood vessel rupture and bleeding (hemorrhagic stroke.

While the initial ischemic event, or primary injury, causes brain tissue damage and cell death, the largest extent of the damage occurs after recanalization of the occluded vessel, also known as reperfusion injury, triggered by excitotoxicity, reactive oxygen species, and subsequently inflammation. Current treatments for ischemia encompass behavioral changes, drug therapy, and/or surgical intervention. Drugs are frequently preferred before resorting to invasive procedures and to provide more immediate relief than long-term behavioral changes.

Domain V's parent molecule, perlecan, is a >400 kDa heparan sulfate proteoglycan consisting of five protein domains (I-V from N to C-terminus), several glycosaminoglycan (GAG) chains, and is a major extracellular matrix (ECM) constituent of basement membranes (BMs)[9]. Perlecan domains III and V have been found in human fetal BM zones of many tissues including brain neuroectoderm and capillaries as early as gestational week six[10]. Furthermore, perlecan plays a critical role in maintaining BM integrity and vasculo- and angiogenesis[11], mediating epithelialization, and in supporting adhesive separation and maintenance of the neuroepithelium in many tissues including the brain[12]. BMs compartmentalize tissues and affect cellular processes including proliferation, migration, and differentiation[10,13]. Importantly, complete perlecan knockout mice (an embryonic lethal deletion) have brain atrophy associated with reduced cell proliferation, hampered migration of neocortical interneurons and cortical plate and subplate neurons during brain development, as well as impaired FGF-2 driven adult neurogenesis[14,15]. Furthermore, full length bovine perlecan has been demonstrated to promote neural stem/progenitor cell proliferation and neuritogenesis in vitro[16]. Collectively, these observations suggest a key role of perlecan in developmental neurogenesis.

Following ischemic stroke, subventricular zone (SVZ) neurogenesis increases and migration of new neurons is redirected from the physiological rostral migratory stream-olfactory bulb pathway towards the stroke damaged area, where neuroblasts provide trophic support and may replace lost neurons. Although very few new neurons reach and survive in the stroke damaged area naturally, there is evidence to support the hypothesis that therapies may be capable of boosting neurogenesis to a level that provides functional improvement[17-21]. Importantly, neurogenesis is causally linked with angiogenesis in neurovascular niches[22] and migration of these newly born neurons is facilitated by blood vessel scaffolds.

Following stroke, extensive ECM and BM remodeling occurs including significant proteolysis. Specifically, perlecan undergoes more extensive and persistent proteolysis after experimental (in rodents and nonhuman primates) stroke than other brain ECM components resulting in robust generation of DV fragments[6,23].

Current standard of care for ischemic stroke is rapid reopening of the occluded brain blood vessel with tissue plasminogen activator (t-PA). Unfortunately, t-PA is limited to a brief window of 4.5 hours within symptom onset contributing, along with other factors, to the exclusion of many patients. Furthermore, results from large t-PA trials have been mixed, showing improving recanalization rates, but no overwhelming improvements in outcome. While the speed and efficacy of recanalization (by the use of tissue plasminogen activator or mechanical clot removal) has improved, patients continue to experience poor outcome, and functional recovery is often limited. Unfortunately, despite the promise of many potential neuroprotective therapies, none have thus far succeeded in clinical trials.

Thus, there remains a critical need for novel stroke therapies that possess a broader therapeutic window and promote post-stroke brain health through multiple mechanisms, including neurorepair.

SUMMARY

The presently-disclosed subject matter meets some or all of the above-identified needs, as will become evident to those of ordinary skill in the art after a study of information provided in this document.

As noted herein, domain V (DV), a protein fragment of the extracellular matrix proteoglycan perlecan, is neuroprotective and restores motor function following experimental stroke. To date, however, neuroprotective stroke therapies are limited by a narrow therapeutic window, may hinder brain repair, and have a dubious track record in clinical translation. As neurogenesis is an important endogenous component of post-stroke repair occurring days to months after stroke, and previous studies have implicated perlecan in developmental neurogenesis, the present inventors sought to determine whether DV could have a therapeutic window by enhancing neurogenesis and synaptic restoration after stroke. As disclosed herein, the present inventors have shown that DV is a clinically relevant neuroprotective and neuroreparative novel stroke therapy with a broad therapeutic window.

The present invention relates to methods of enhancing recovery after ischemic injury in a subject, comprising: administering to a subject in need thereof an effective amount of DV.

The present invention further relates to a method wherein the administering DV increases neurogenesis, increases neuron survival, improves functional recovery, improves motor function, increases outgrowth of new neurons, restores excitatory synaptic transmission, reverses ischemic induced changes to excitatory post synaptic currents, increases neurosphere expansion, and/or increases neuroblast migration compared to a control subject that does not receive DV.

Some embodiments include a method wherein the DV is administered more than 24 hours after the ischemic event. In some embodiments, DV is administered 2, 3, 4, 5, 6, 7, 8, 9, or 10 days after the ischemic event. In some embodiments, DV is administered about 24 hours to about 7 days after the ischemic event.

In some embodiments, in addition to affecting neuroprotection and angiogenic neurorepair, the method affects neurogenic neurorepair. In some embodiments, the method involving administration of DV affects multiple aspects of neurogenesis, including, for example, proliferation of neuronal precursor/neural stem cells, differentiation of these cells into neurons, migration of these cells, neurite extension from neurons, and synaptogenesis (new neuronal connections).

Other embodiments of the present invention relate to a method wherein the ischemic injury is a photothrombic stroke or a transient middle cerebral artery occlusion stroke.

Some embodiments include a method wherein the administering step includes administering about 0.5 mg/kg to about 20 mg/kg of the DV.

Other embodiments of the present invention relate to a method wherein neural precursor cells, new post-stroke mature neurons peri-infarct neurite density is increased.

Some embodiments include a method wherein the administering is performed intravenously or intraperitoneally.

The present invention further relates to a method of enhancing neurorepair in a subject in need comprising: administering DV to the subject.

Some embodiments include a method wherein the subject has had a traumatic brain injury or stroke.

Other embodiments of the present invention relate to a method wherein the administering occurs daily for a period of 1 day to two weeks.

Some embodiments include a method wherein the administering DV increases neurogenesis, increases neuron survival, improves functional recovery, improves motor function, increases outgrowth of new neurons, restores excitatory synaptic transmission, reverses ischemic induced changes to excitatory post synaptic currents, increases neurosphere expansion, and/or increases neuroblast migration compared to a control subject that does not receive DV.

The present invention further relates to a method wherein the subject is a mammal.

In other embodiments of the present invention, the subject is a mouse or a human.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

BRIEF DESCRIPTION OF THE DRAWINGS

Illustrative aspects of embodiments of the present invention will be described in detail with reference to the following figures wherein:

FIGS. 1A-1D are representative immunohistochemical analysis of domain V in human brain tissue from control (FIGS. 1A and 1B) or old infarcted regions at <2 days (FIGS. 1C and 1D), 7 days (FIGS. 1E and 1F), and 90 days (FIGS. 1G and 1H), scale bar=200 μm.

FIG. 2A includes representative images of doublecortin (DCX) brain immunofluorescence with DAPI nuclear counterstain from PSD 14 young perlecan/DV deficient (pln−/−) or wild-type (WT) mice subjected to tandem transient CCA/MCA occlusion showing the area encompassing the subventricular zone (SVZ). Arrowheads represent areas of DCX positive staining. * represents lateral ventricle. Scale bar=100 μm. FIG. 2B includes quantification of DCX positive pixels as in FIG. 1A, demonstrating that pln−/− mice had significantly less neurogenesis in the SVZ after stroke. n=5 per group. P values were assessed by Student's t-test. **p<0.01 Data represent mean+/−SEM.

FIG. 3A illustrates rotor rod behavioral task quantification of distance (cm) travelled on the rod and FIG. 3B illustrates grip strength (g) behavioral task for mice given either PBS vehicle control or recombinant DV initiated 7 days (dashed line) after CCA/MCAo stroke. n=6 per group. FIG. 3C includes representative images from H&E stained coronal brain sections 21 days after injury showing 10× images (left) and 25× images (right) where the blue boxes represent regions of interest (ROI) and where the red outline represents areas identified as dysmorphic for hematoxylin positive pixel quantification. n=7 per group. Scale bar=100 μm. FIG. 3D includes quantification of dysmorphic area ($μm^2$), defined by cellular loss/decreased cell and tissue density, smaller, irregular shaped nuclei or irregular tissue patterning from surrounding areas from 10× images. FIG. 3E. includes quantification of hematoxylin positive pixels from 25× images. P values were assessed by 2 way RM ANOVA followed by Tukey's post-hoc test (FIGS. 3A and B) and by Student's t-test (FIGS. 3D and E). *p<0.05, **p<0.01 Data represent mean+/−SEM FIG. 4A includes representative images of DCX staining within the peri-infarct region on PSD 21 from PBS vehicle and DV treated young mice following CCA/MCAo. DAPI staining shows overall cellular staining. Scale bar=50 μm. FIG. 4B includes quantification of DCX positive cells showing the delayed DV treatment significantly increases neurogenesis in the ipsilateral brain of stroked mice. Data are % of PBS vehicle and represent mean+/−SEM.

FIG. 4C includes representative images of BrdU and NeuN co-staining within the stroked area from PBS vehicle and DV treated mice 21 days following CCA/MCAo. Scale bar=50 μm.

FIG. 4D includes quantification of BrdU/NeuN co-labeled cells showing that DV treatment significantly increases the number of new, mature neurons n=6 (PBS) and n=6 (DV). P values were assessed by Students t-test *p<0.05 **p<0.01 Data represent mean+/−SEM.

FIG. 5A illustrates the experimental design and includes a schematic depicting the location of recorded L2/3PCs from mice given sham-injury, transient MCAo stroke injury with control vehicle treatment (PBS Vehicle) and with DV treatment (DV Treated). FIG. 5B includes representative traces of spontaneous excitatory post-synaptic currents (sEPSCs) for L2/3PCs. FIG. 5C shows that the frequency of sEPSCs was significantly elevated by MCAo stroke injury and this effect was reversed by DV treatment. FIG. 5D shows that sEPSC amplitude was not affected by this injury with vehicle or DV Treatment. FIG. 5E includes representative traces of miniature excitatory post-synaptic currents (mEPSCs) for L2/3PCs. FIG. 5F illustrates that CCA/MCAo stroke injury increased mEPSC frequency and this effect was reversed by Domain V treatment. FIG. 5G illustrates that mEPSC amplitude was not affected by this injury with vehicle or DV Treatment. P values were assessed by 1-way ANOVA followed by Tukey's post-hoc test.* $p<0.05$ relative to sham-injury. Data represent mean±SEM. n=5

FIG. 6A includes the results of neurosphere expansion assays showing representative phase contrast images of media only, PBS vehicle, and DV (300 nM) conditions as labeled 1, 2, 3, and 4 days after plating (DAP) from neurosphere-dissociated cells in suspension. Scale bar=140 μm. FIG. 6B illustrates quantification of neurosphere diameter (um), showing significantly increased neurosphere size by DAP2 in the DV condition compared to media only (dashed line) and PBS vehicle control. n=3. FIG. 6C includes the results of MTS proliferation assays quantifying that DV treated cells had significantly increased enzymatically-active cell proliferation compared to the media only (dashed line) and PBS vehicle control. n=5. FIG. 6D includes representative images of neurosphere migration assays after 30 minutes and 6 hours showing that an α2 function blocking antibody (nAb) reduced the migration of NPCs and DV could not increase migration in the presence of the α2 nAb. Scale bar=140 μm. FIG. 6E includes quantification of the migration distance out of neursopheres, as in FIG. 6D, compared to PBS vehicle conditions (dashed line). n=5 FIG. 6F includes qPCR results demonstrating that DV significantly increases α2 gene expression compared to PBS vehicle conditions (dashed line). The α2 nAb blocked α2 gene expression and DV was unable to reverse this effect. n=9 P values were assessed by using 2-way RM ANOVA followed by Bonferroni's post-hoc test, 1-way ANOVA followed by Tukey's post-hoc test and Student's t-test where appropriate. Statistical bar represents comparison of the 2 groups at its endpoints in all figures. *p<0.05, p<0.01, *p<0.001 in all figures and data represent mean+/−SEM.

FIG. 7A includes immunocytochemistry double labeling of neuron-specific βIII tubulin with DAPI nuclear counterstain, showing representative images of various treatment conditions as labeled. Scale bar=100 μm. FIG. 7B includes quantification of treatment, which greatly increased neuronal differentiation. Media only condition (dashed line) used as a control and set to 100%. n=3 FIG. 7C shows qPCR quantification showing DV increases DCX gene expression compared to PBS vehicle (dashed line), treatment with α2 nAb decreases DCX gene expression, and DV had no effect in reversing this α2 nAb mediated decrease in DCX expression. FIG. 7D shows the results of neurite extension assays showing representative light microscopy images of E16 mouse cortical neurons treated as labeled. Primary neurons were fixed 4 hours after treatment and stained with cresyl violet. Arrows indicate examples of neurites. Scale bar=10 μm. FIG. 7E shows quantification (y-axis) of number of neurites, FIG. 7F shows quantification of neuritesnumber of cell-cell connections per field, and FIG. 7G shows quantification of the number of cells with one or more neurites, showing enhanced neurite extension and connectivity with DV treatment, which was blocked in the presence of the α2 integrin blocking antibody. n=5 FIG. 7H shows cortical neurons (TuJ1) from post-natal days 5-6 mice, which were seeded in vitro onto either mature control (control) or stretch-reactive (stretch) astrocytes (GFAP; DAPI). Arrows show the position of the soma while arrowheads represent neurites. Scale bar=100 μm The process of neurite outgrowth was inhibited when the cortical neurons were plated onto stretched astrocyte compared to controls (dashed line reflects PBS Control condition). Neurite outgrowth however was more vigorous when cortical neurons were plated onto either control or stretched astrocytes in the presence of DV (300 nM) when compared to PBS treated controls. n=3. P values were assessed using 1-way ANOVA followed by Tukey's post-hoc test. *p<0.05 p<0.01 and *p<0.001 in all figures and data represent mean+/−SEM FIGS. 8A-8K illustrate that domain V (DV) increases neuroblast migration and MAP2 staining after stroke that is inhibited in the absence of α2-integrin activity. FIG. 8A includes representative photomicrograph of DCX, DAPI immunofluorescence of ipsilateral brain tissue taken from the dorsal lateral aspect of the LV (indicated by *) on PSD 42 after photothrombotic stroke, treated as labeled. FIGS. 8B and 8C include graphs representing cylinder (FIG. 8B) and grid walking (FIG. 8C) behavioral tests. FIG. 8D includes a sample photomicrograph illustrating the regions where cells were counted, as shown in FIGS. 8E and 8F. Quantification of average cell counts are shown in FIG. 8E, Region A is next to the LV including the bottom half of the corpus callosum (CC), and FIG. 8F, Region B that includes the top half of the CC and surrounding the stroke cavity. FIG. 8G includes representative images depicting MAP2 and DAPI immunofluorescence in the brains of α2 or decoy antibody treated animals with or without DV treatment. Boxes (150 μm square) show the regions of interest within the pen-infarct that were subjected to analysis from either layer 2/3 (regions 1 & 2) or layer 5 (regions 3 & 4). FIG. 8H includes quantification of MAP2 staining within peri infarct from regions 1-4 (n=8 per group; data are expressed over cell density). FIG. 8I includes a representative photomicrograph and FIG. 8J includes quantification of DCX stains from WT and from α2 KO animals following stroke. FIG. 8K is a graphic summary showing Domain V's effects on post stroke neurogenesis. DV increases NPC proliferation at the SVZ. Domain V acts through α2β1 integrin to increase neuroblast migration out of the SVZ into the stroke affected area. DV enhances neuronal differentiation and neurite extension through α2β1 integrin in the stroke affected area.

DV's effects on migration, differentiation, and neurite extension are abolished upon α2 blockade. (Not graphically represented) DV restores excitatory synaptic drive to stroke affected cortical regions. All scale bars=200 µm. n=5 for WT condition and n=3 per α2 KO condition P-values were assessed using Student's t-test for 2 group comparisons or One-way ANOVA followed by Tukey's post-hoc test for 3 or more conditions at a single time point. * p<0.05, ** p<0.01 and $ p<0.001 compared to PBS+IgG controls and +p<0.05 and ^p<0.001 compared to DV+decoy antibody controls. For 3 or more conditions at multiple time points, Two-way ANOVA with repeated measures were used (DV+Decoy & p<0.05 compared to the other three conditions), * p<0.05 compared to PBS+decoy antibody controls (days 14 and 42) and #p<0.05 compared to DV+α2 nAb (day 28).

Figure 9A:
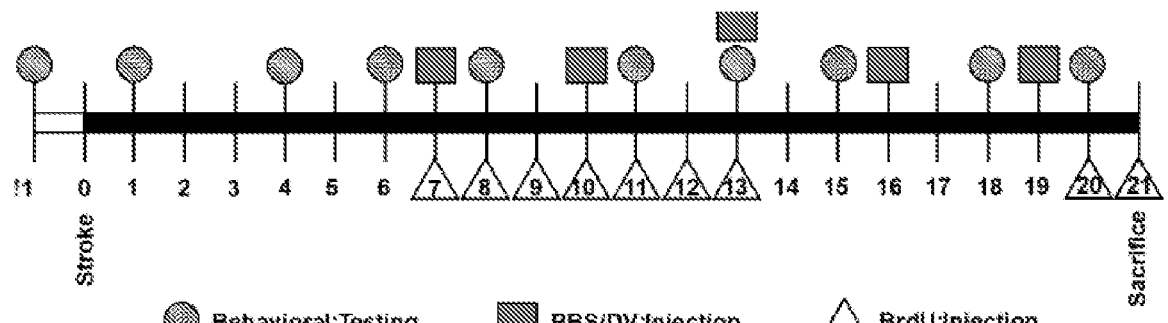
Figure 9B:
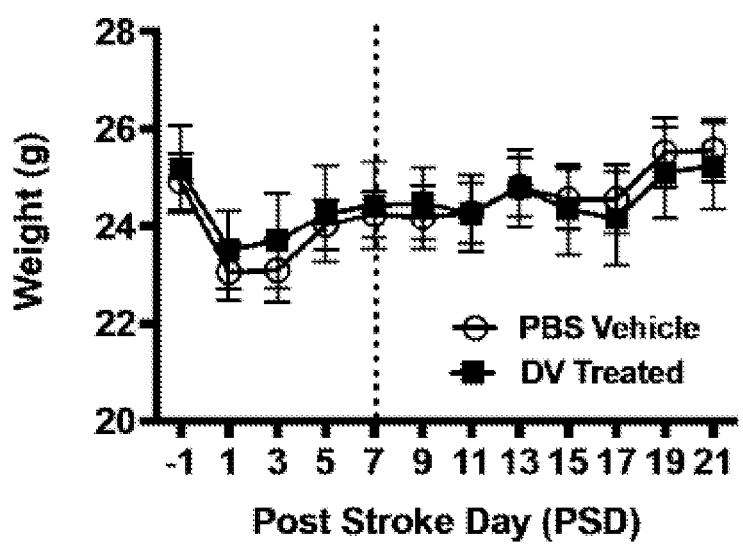

FIGS. 9A and 9B include an experimental timeline (FIG. 9A) and animal weights (FIG. 9B) for a DV MCAo study.

Figure 10A:
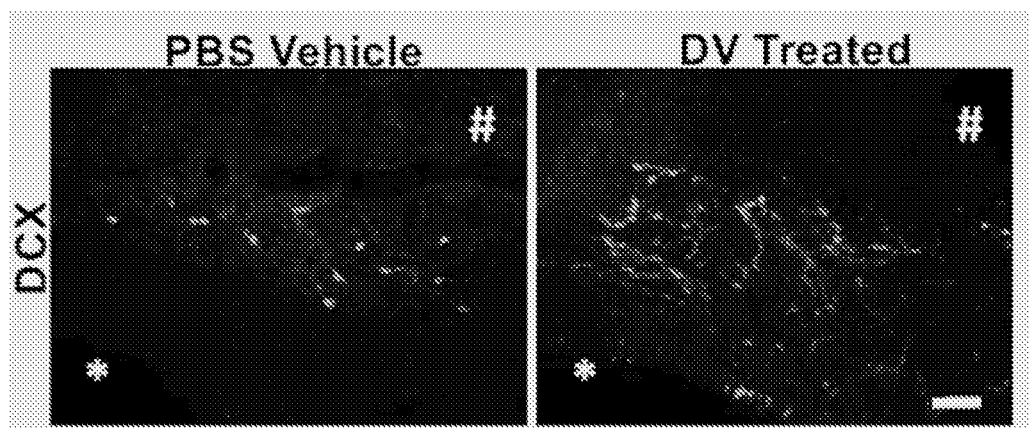
Figure 10B:
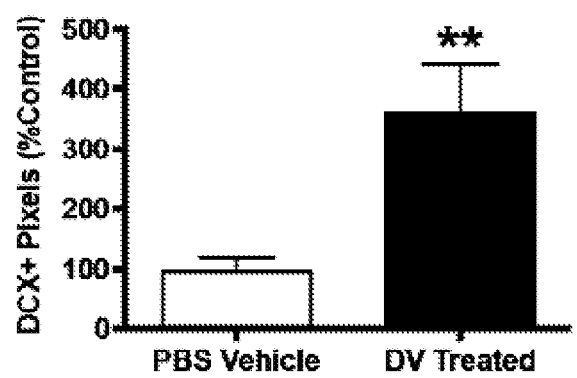

FIGS. 10A and 10B illustrate that domain V increases the number of DCX positive neurons in aged mice. FIG. 10A includes representative images of DCX from PSD 7 aged mice subject to photothrombotic stroke showing the area encompassing the subventricular zone (SVZ) lining the lateral ventricle (indicated with an *) and the infarct region (indicated with a #). Scale bar=50 µm FIG. 10B includes quantification of DCX positive cells showing the delayed DV treatment significantly increases neurogenesis in the ipsilateral brain and SVZ of stroked mice. n=6 per group. P values were assessed by Student's t-test. **p<0.01 Data are % of control and represent mean±SEM.

Figure 11A:
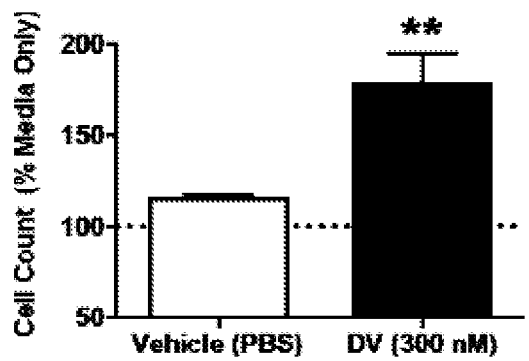
Figure 11B:
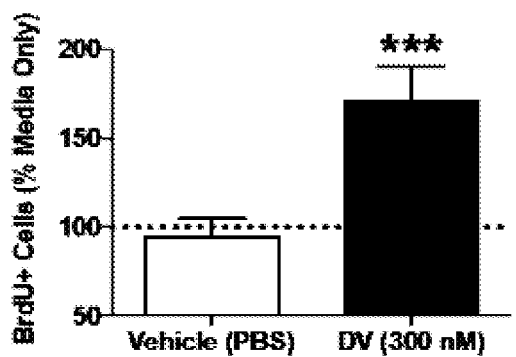
Figure 11C:
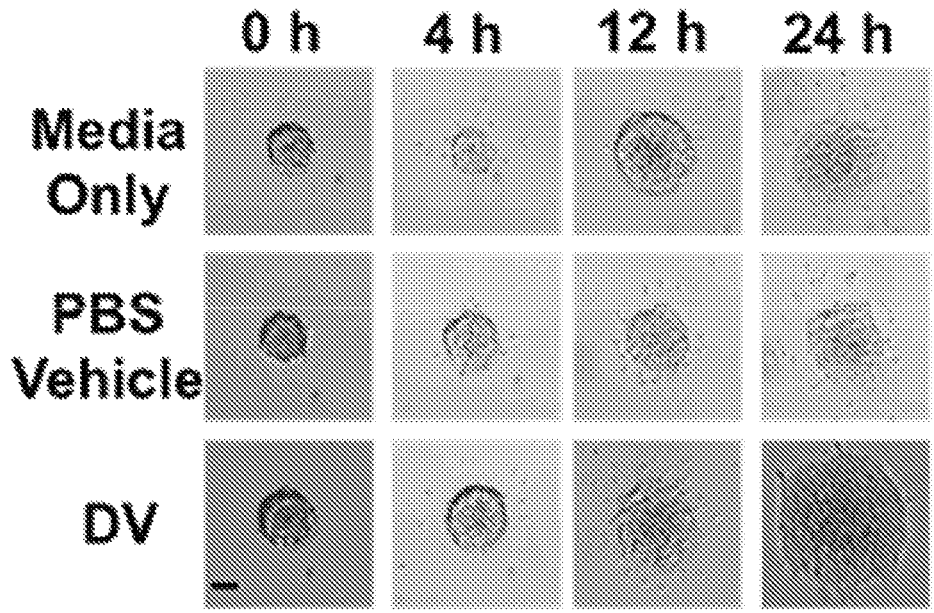
Figure 11D:
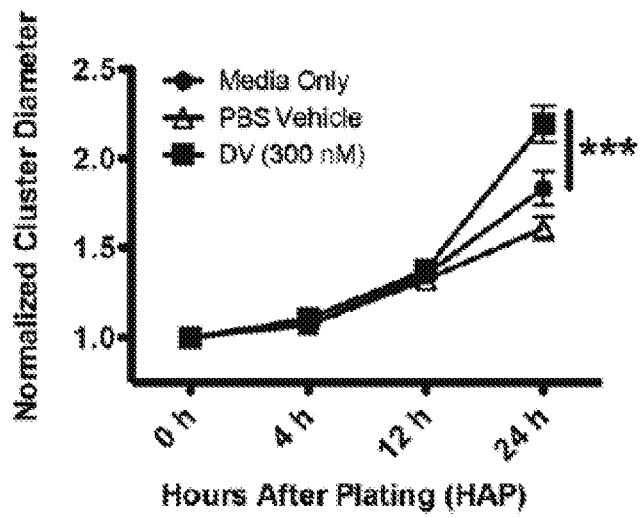
Figure 11E:
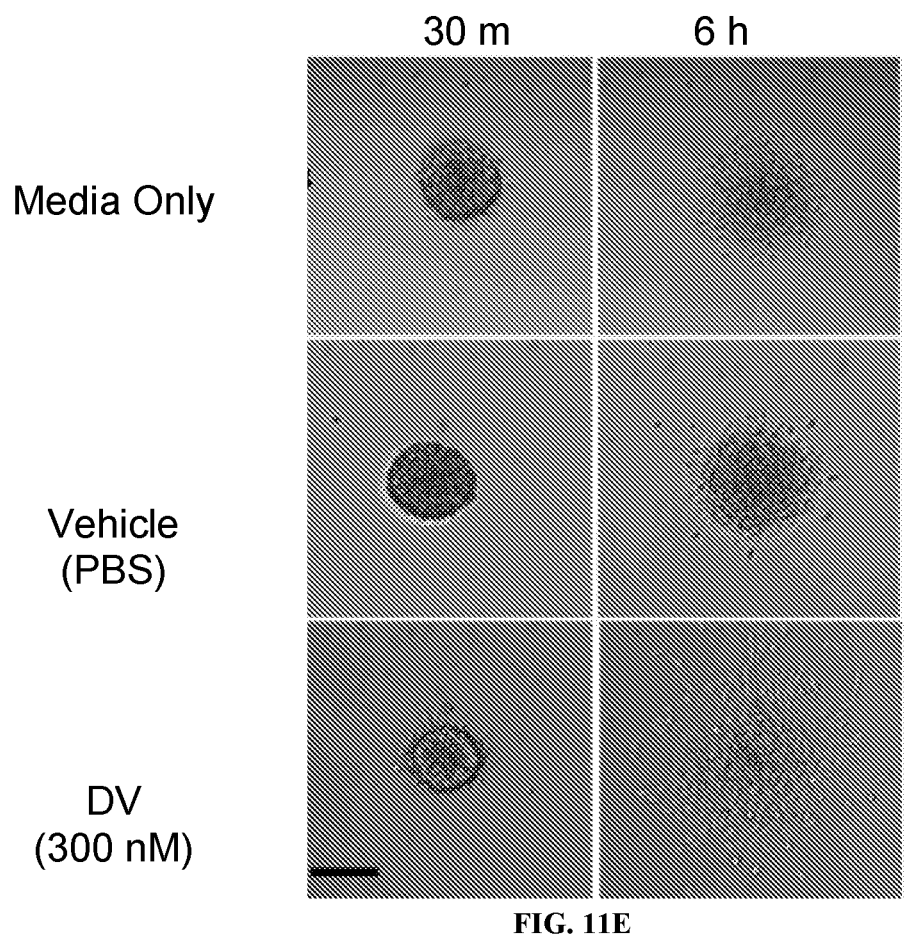
Figure 11F:
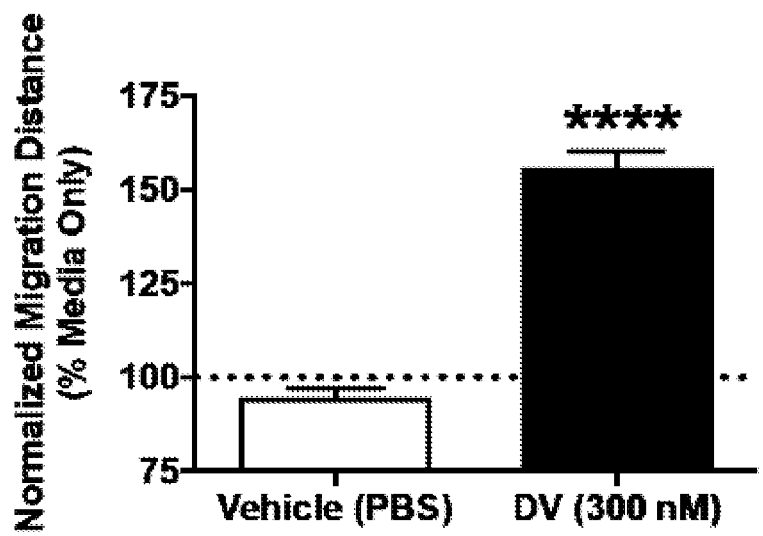

FIG. 11A-11F illustrate that domain V increases neurosphere expansion on standardized matrices in vitro. FIG. 11A includes trypan blue exclusion cell counts quantifying that the DV condition had significantly increased numbers of viable cells, cultured as neurospheres, compared to the media only (dashed line) and PBS vehicle control. n=5 FIG. 11B illustrates quantification of percent BrdU positive cells, with total cells determined by DAPI, showing increased proliferation and new cells with DV treatment compared to PBS vehicle and heat-inactivated DV control conditions. n=5. Media only conditions set to 100% (dashed line). FIG. 11C shows that DV significantly increased migration out of neurospheres coated on PDL 24 hours after plating compared to media only conditions as shown in these representative phase contrast images. Scale bar=140 µm. FIG. 11D illustrates quantification of normalized cluster diameter of neurosphere at 0, 4, 12, and 24 hours after plating. n=5 FIG. 11E includes representative images of neurospheres plated on PDL/laminin showing increased migration within 6 hours. Scale bar=140 µm. FIG. 11F includes quantification of normalized migration distance out of neurospheres after 6 hours. n=5. P values were assessed by using 2-way RM ANOVA followed by Bonferroni's post-hoc test, 1-way ANOVA followed by Tukey's post-hoc test and Student's t-test where appropriate. Statistical bar represents comparison of the 2 groups at its endpoints in all figures. p<0.01, *p<0.001 ****p<0.0001 in all figures and data represent mean+/−SEM.

Figure 12A:
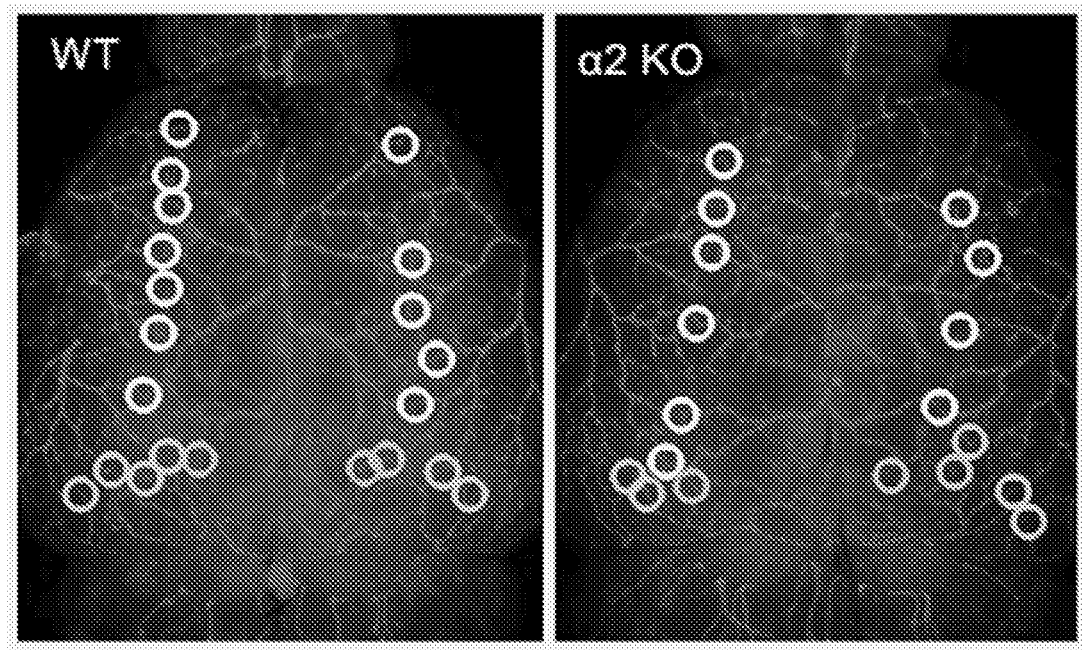
Figure 12B:
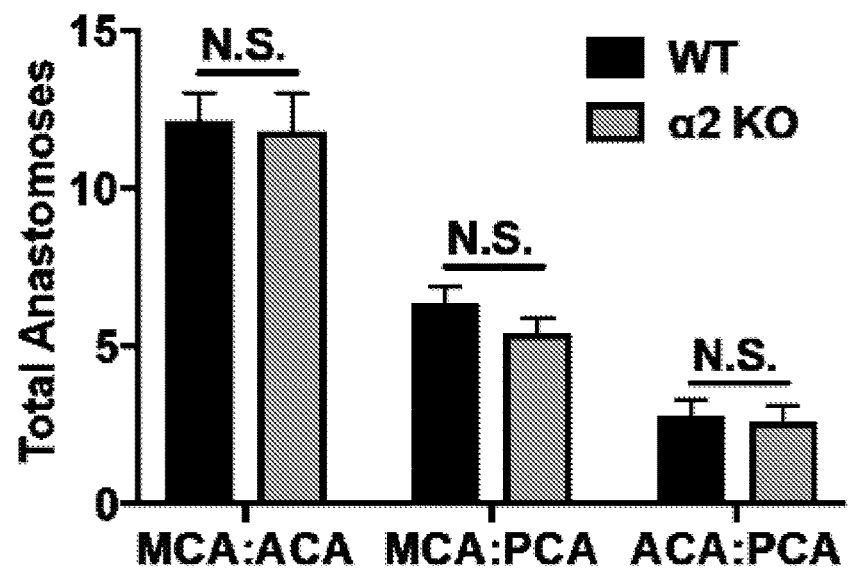
Figure 12C:
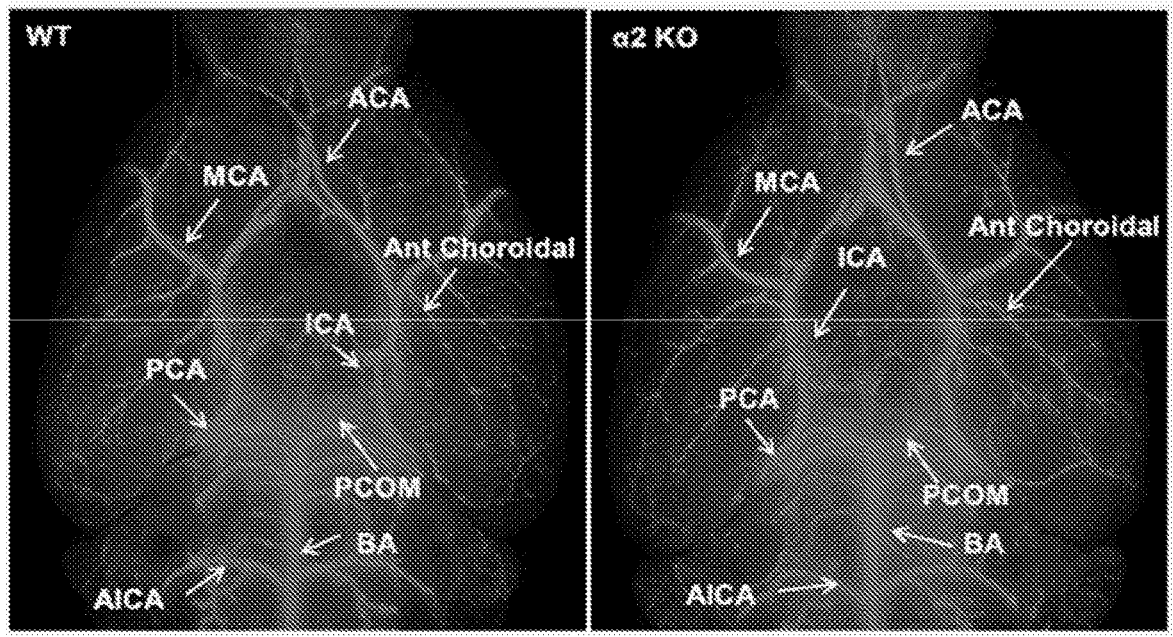

FIGS. 12A-12C illustrate that the vascular anatomy of α2 KO mice is normal as compared to WT mice. FIG. 12A includes dorsal images of whole brains perfused with DiI under 1× magnification and stitched together. White circles identify anastomoses between the middle and anterior cerebral arteries, anastomoses between the middle and posterior cerebral arteries, and anastomoses between the anterior and posterior cerebral arteries. FIG. 12B includes quantification of total anastomoses of each arterial pair showing no significant difference in any group (MCA:ACA p=0.7978; MCA:PCA p=0.2029; and ACA:PCA p=0.7845). FIG. 12C includes ventral images of whole brains at the Circle of Willis showing similar vascular anatomy. α2 KO mice are not missing any of major COW contributors.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

The presently-disclosed subject matter is directed to improving recovery and/or treating ischemia damage with methods that involve use of DV. As is known in the art, ischemia can lead to barrier to neurorepair in a subject. As disclosed herein DV administration, even with a delay of up to 7 days, after experimental stroke improves recovery via increased neurogenesis, survival and outgrowth of these new neurons in manner that restores synaptic connectivity in a key input layer with neocortex. The presently disclosed subject matter shows that DV is a clinically relevant neuroprotective and neuroreparative novel stroke therapy with a broad therapeutic window. Additionally, because of the neuroprotective effects of DV, the presently disclosed methods could find use in other applications where neuroprotection, neurorepair, and/or neurogenesis is needed, such as, for example, traumatic brain injury.

A method of improving recovery after ischemic stroke in a subject is provided including the step of administering an effective amount of DV to a subject. In some embodiments, the administering of DV increases neurogenesis, increases neuron survival and/or increases outgrowth of new neurons compared to a control subject that does not receive DV. The DV can be administered immediately subsequent to a stroke or traumatic brain injury, or can be delayed from about 4 hours to about 7 days after the stroke event. In some embodiments, the administering is performed intravenously or intraperitoneally and is administered at a rate of about 1 mg/kg to about 50 mg/kg, about 1 mg/kg to about 20 mg/kg, or about 1 mg/kg to about 5 mg/kg.

In some embodiments, the subject is a mouse and the stroke is a photothrombic or a transient middle cerebral artery occlusion stroke. In other embodiments, the subject is human. In some embodiments, the stroke can be hemorrhagic, ischemic, or transient ischemic attack (TIA).

In some embodiments, neurogenesis, neurorepair and/or neuroprotection can be measured by an increase in neural precursor cells, new post-stroke mature neurons, and/or peri-infarct neurite density. In some embodiments, measurements of such indicators can determine effectiveness of treatment, need for additional treatment, and/or diagnosis/ prognosis in a subject. In such instances, effectiveness can be determined relative to a control, wherein DV is not administered and/or placed in contact with the target. In some embodiments, a decrease or increase relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease or increase. Measurements of such enhancement, improvement or increase of such indicators can occur from about 1 day to about 60 days post-stroke. In some embodiments, from about 10 to about 30 days.

The administration of DV can be acute or over time. In some embodiments, the administering occurs at least once daily for a period of 1 day to two weeks. In other embodiments, the DV can be administered twice a day or every two days. Optimization of dosing regimen and dosing amounts is well within the skill of the art area.

In some embodiments, a method is provided for treating the effects of ischemia in a cell, wherein the ischemia may be caused by one or more ischemic events. In some embodiment the method includes contacting the cell with DV. The term "contacting" as used herein refers to any means by which DV is brought into sufficient proximity and/or in direct contact with a cell such that the cell is capable of receiving the DV. For instance, in some embodiments contact refers to coating a cell with an DV. In other embodiments contact refers to culturing a cell in a solution that includes DV. In other embodiments the cell is within a subject, and contact refers to administering an DV to the subject such that a cell within the subject is capable of receiving DV.

The term "enhancing" as used herein refers to the characteristic of increasing or improving recovery associated with ischemia and/or brain injury, which can include increasing neurogenesis, neurorepair and/or neuroprotection. The term "enhancing" does not imply a particular degree of increasing or improving recovery associated with ischemia and/or brain injury. Likewise, the term "enhancing" does not imply that side effects due to ischemia and/or brain injury are eliminated. The term "enhancing" can refer to a reduction in the resulting side effects from ischemia and/or brain injury, including improving neuroprotection, functional recovery and/or neurogenesis, by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% relative to a control that has not been contacted or treated with DV.

Functional recovery can be measured in several ways, including assessments of motor function. One exemplary model utilized and well-known in the art is the use of the Disability Rating Scale (DRS) wherein Disability-free recovery (DFR) is defined as a score of zero on the Disability Rating Scale (DRS), and where a score with a smaller value is an improvement in functional recovery.

With respect to methods for preventing ischemia in a cell, in some embodiments the cell is a brain cell. In other embodiments the cell is part of a particular tissue, and the method includes preventing ischemia in the cell(s) of the tissue. In this respect, the term "tissue" is used herein to refer to a population of cells, generally consisting of cells of the same kind that perform the same or similar functions. The types of cells that make the tissue are not limited. In some embodiments tissue is part of a living organism, and in some embodiments tissue is tissue excised from a living organism or artificial tissue. In some embodiments tissue can be part of an organ, wherein the term "organ" refers to a part of a subject which is composed of several tissues and adapted to perform a specific function or functions, such as the brain.

The presently-disclosed subject matter also relates to methods for treating ischemia in a subject. In some embodiments the method comprises administering to the subject an effective amount of DV.

The term "administering" refers to any method of providing DV and/or pharmaceutical composition thereof to a subject. Such methods are well known to those skilled in the art and include, but are not limited to, oral administration, transdermal administration, nasal administration, intracerebral administration, and administration by injection, which itself can include intravenous administration, intra-arterial administration, intramuscular administration, subcutaneous administration, intravitreous administration, intracameral (into anterior chamber) administration, and the like. Administration can be continuous or intermittent. In various aspects, a preparation can be administered therapeutically; that is, administered to treat an existing disease or condition (e.g., ischemia, infarction, etc.). In other instances a preparation is administered prophylactically; that is, administered to prevent or treat a disease or condition that may otherwise develop. In some embodiments, the administration is intra-arterially or intravenously.

As used herein, the terms "effective amount" and "therapeutically effective amount" are used interchangeably and mean a dosage sufficient to provide treatment. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

In some instances an effective amount is determined relative to the weight of a subject, and can be selected from dosages of about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, and 50 mg/kg. In some preferred embodiments, about 0.5 mg/kg to about 20 mg/kg.

The term "subject" is used herein to refer to a target of administration, which optionally displays symptoms related to a particular disease, pathological condition, disorder, or the like. Thus, in some embodiments a subject refers to a target that displays symptoms of ischemia and/or brain injury. The subject of the herein disclosed methods can include both human and animal subjects. A subject can be, but is not limited to, vertebrates, such as mammals, fish, birds, reptiles, or amphibians. More specifically, the subject of the herein disclosed methods can include, but is not limited to, a human, non-human primate, cat, dog, deer, bison, horse, pig, rabbit, dog, sheep, goat, cow, cat, guinea pig, or rodent. The term does not denote a particular age or sex. Adult and newborn subjects, as well as fetuses, whether male or female, are intended to be covered. The term "subject" includes human and veterinary subjects.

The terms "treat," "treatment," and the like refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylatic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

In some methods of administration, the ischemia is caused by a particular ischemic event. In some instances, the ischemia is caused at least in part by an ischemic event selected from cerebral ischemia, stroke, and a combination thereof. In some methods of administration, the reduction in brain function is from traumatic brain injury. In some embodiments the DV is administered one or more times during or after the onset of ischemia and/or during or after an ischemic event and/or brain injury. In this respect, in some embodiments DV is administered one or more times during or after the onset of two or more distinct ischemic events, and therefore the present methods are not limited to a single administration of DV. In such embodiments, DV can optionally be administered immediately after or about 0.1, 0.25, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 hours, 4 days, 5 days 6 days, 7 days, 8 days 9 days, 10 days, 11 days, 12 days, 13 days, or 14 days after the onset of the ischemic event.

The terms "diagnose" and the like as used herein refer to methods by which the skilled artisan can estimate and even determine whether or not a subject is suffering from a given disease or condition, such as ischemia. Along with diagnosis, clinical "prognosis" or "prognosticating" is also an area of great concern and interest, and the terms "prognose" and the like refer to act of determining the relative risk associated with particular conditions in order to plan the most effective therapy. If an accurate prognosis can be made, appropriate therapy, and in some instances more effective therapy, for the subject can be chosen.

Those of ordinary skill in the art will recognize factors and methods for diagnosing and/or prognosing a subject with ischemia. Factors that can contribute to a diagnosis and/or prognosis of ischemia in a subject include, but are not limited to, hypercholesterolemia, electrocardiogram (EKG) changes associated with a risk of or the presence of ischemia (e.g., peaked or inverted T-waves or ST segment elevations or depression in an appropriate clinical context), sedentary lifestyles, angiographic evidence of partial coronary artery obstruction, evidence of a cerebrovascular accident CVA, and other clinical evidence of ischemia. Similarly, brain injury can be assessed in several ways, including neuropsychological test, utilization of the Glasgow Outcome Scale (GOS) or the DRS, CT scans and other imaging modalities, and blood tests such as measuring levels of brain-derived neurotrophic factor (BDNF).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a neurosphere" includes a plurality of such neurospheres, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The present invention relates to methods of enhancing recovery after ischemic injury in a subject, comprising: administering to a subject in need thereof an effective amount of DV.

The present invention further relates to a method wherein the administering DV increases neurogenesis, increases neuron survival, improves functional recovery, improves motor function, increases outgrowth of new neurons, restores excitatory synaptic transmission, reverses ischemic induced changes to excitatory post synaptic currents, increases neurosphere expansion, and/or increases neuroblast migration compared to a control subject that does not receive DV.

Some embodiments include a method wherein the DV is administered about 4 hours to about 20 days after the ischemic event.

Other embodiments of the present invention relate to a method wherein the ischemic injury is a photothrombic stroke or a transient middle cerebral artery occlusion stroke.

Some embodiments include a method wherein the administering step includes administering about 0.5 mg/kg to about 20 mg/kg of the DV.

Other embodiments of the present invention relate to a method wherein neural precursor cells, new post-stroke mature neurons pen-infarct neurite density is increased.

Some embodiments include a method wherein the administering is performed intravenously or intraperitoneally.

The present invention further relates to a method of enhancing neurorepair in a subject in need comprising: administering DV to the subject.

Some embodiments include a method wherein the subject has had a traumatic brain injury or stroke.

Other embodiments of the present invention relate to a method wherein the administering occurs daily for a period of 1 day to two weeks.

Some embodiments include a method wherein the administering DV increases neurogenesis, increases neuron survival, improves functional recovery, improves motor function, increases outgrowth of new neurons, restores excitatory synaptic transmission, reverses ischemic induced changes to excitatory post synaptic currents, increases neurosphere expansion, and/or increases neuroblast migration compared to a control subject that does not receive DV.

The present invention further relates to a method wherein the subject is a mammal. In other embodiments of the present invention, the subject is a mouse or a human.

The presently-disclosed subject matter is further illustrated by the following specific but non-limiting examples. The examples may include compilations of data that are representative of data gathered at various times during the course of development and experimentation related to the presently-disclosed subject matter. Furthermore, some of the examples described herein may be prophetic examples.

EXAMPLES

As illustrated by the studies summarized in these Examples, DV is chronically increased in the brains of human stroke patients, suggesting that it is present during post-stroke neurogenic periods. It was determined that perlecan deficient mice had significantly impaired neurogenesis after experimental stroke (transient middle cerebral artery occlusion stroke, MCAo). It was shown that I.P. administered human recombinant DV enhanced neurogenesis after stroke in young and aged wild-type (WT) mice in two distinct stroke models (MCAo and permanent photothrombotic occlusion). Specifically, administration of DV 6 hours after photothrombotic stroke or 7 days after MCAo significantly increased the number of immature neuroblasts and new mature neurons in the stroke affected area, improved long-term motor function, and restored peri-infarct excitatory synaptic drive to neocortical layer 2/3 pyramidal neurons. In vitro, DV increased mouse neural precursor cell proliferation, migration, neuronal differentiation, and neurite extension. Furthermore, DV's effects were inhibited by blockade of the extracellular matrix receptor $\alpha 2\beta 1$ integrin in stroked WT mice, as well as in $\alpha 2\beta 1$ integrin knockout mice (which also had reduced endogenous post-stroke neurogenesis), suggesting that DV's neurogenic effects depend on the $\alpha 2\beta 1$ integrin and suggests that $\alpha 2\beta 1$ integrin has a significant role in neurogenesis. Collectively, these results demonstrate that perlecan plays a previously unrecognized role in post-stroke neurogenesis and that delayed DV administration after experimental stroke improves recovery. This mechanism occurs in an $\alpha 2\beta 1$ integrin-dependent manner via increased neurogenesis, survival and outgrowth of these new neurons, and improved synaptic neocortical connectivity. These results suggest that DV is a clinically relevant neuroprotective and neuroreparative novel stroke therapy with a broad therapeutic window.

Example 1: Delayed Administration of DV Promotes Functional Recovery and Reduces Histological Damage Following Mechanical Experimental Stroke Human recombinant DV treatment (2 mg/kg, or PBS vehicle control) was given by intraperitoneal (I.P.) injection beginning on PSD 7 and dosed every third day until PSD 19 and mice were euthanized on PSD 21. The complete experimental timeline is shown in FIG. 9A. Vehicle was used as an appropriate control for DV administration as repeated prior in vivo stroke studies with heat-inactivated DV demonstrated that it had no effect on animal vital signs, blood gases, electrolytes, infarct volume or angiogenic neurorepair[6]. DV treatment was delayed until PSD 7 in order to determine whether it could have a broad therapeutic window for experimental stroke as well as in an attempt to distinguish potential DV effects on neurorepair mechanisms from more acute (e.g. to PSD 3) neuroprotective effects that the present inventors demonstrated in this experimental stroke model[6]. This delayed DV treatment paradigm had no adverse effect on mouse weights (FIG. 9B) or other observable signs of animal distress (fur ruffling, diminished activity, etc.), suggesting that long-term (~2 week) DV administration did not adversely affect mouse health.

Figures 1A, 1B, 1C, 1D, 1E, 1F, 1G, 1H, 1I:
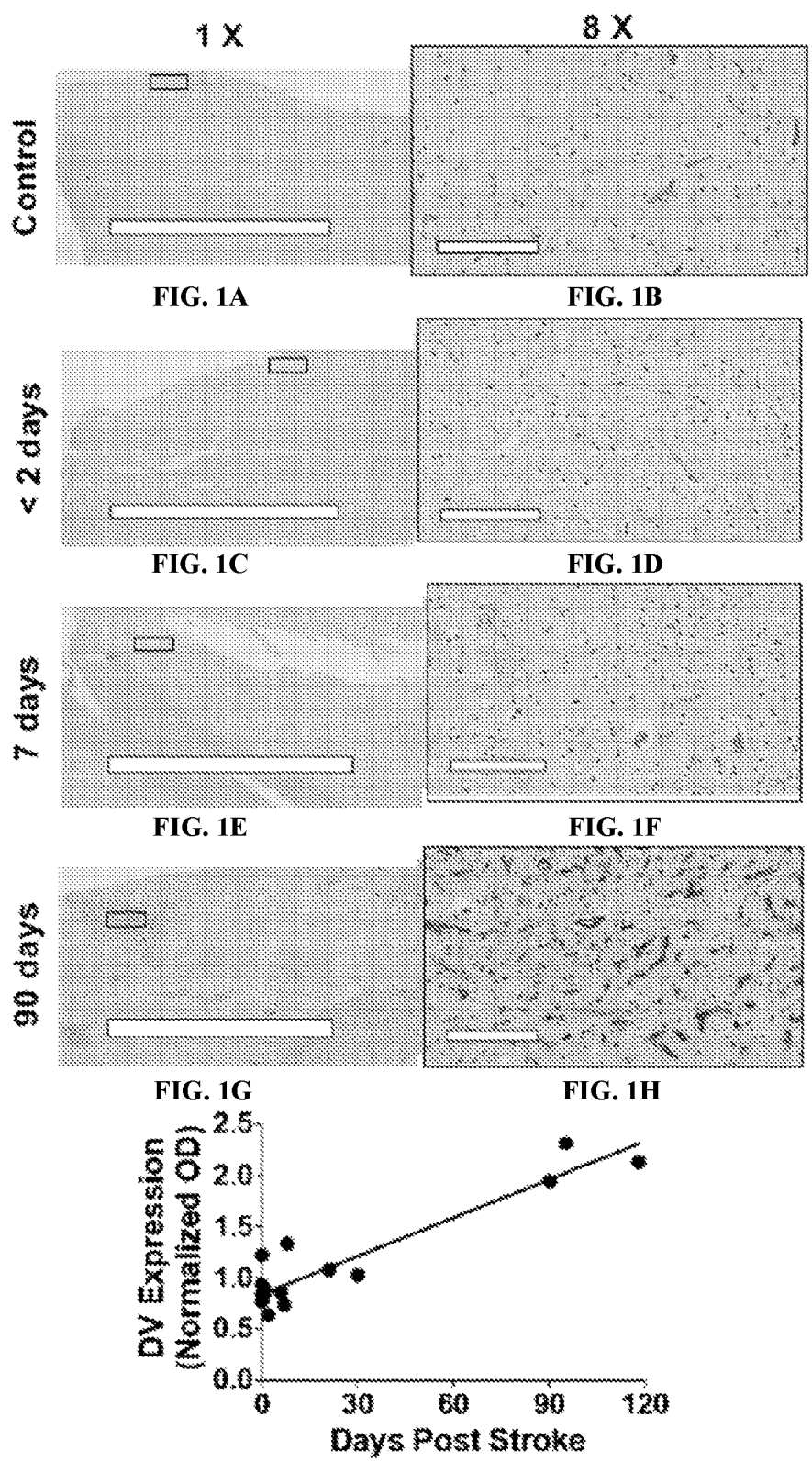
FIGS. 1A-1H illustrate that domain V (DV) expression is increased chronically in human stroke brain tissue.
FIG. 1I is a graph representing domain V expression in human brains collected from controls at various time points following stroke, n=14. The solid line represent linear regression, $R^2$=0.7837, p<0.0001.
Figure 2A:
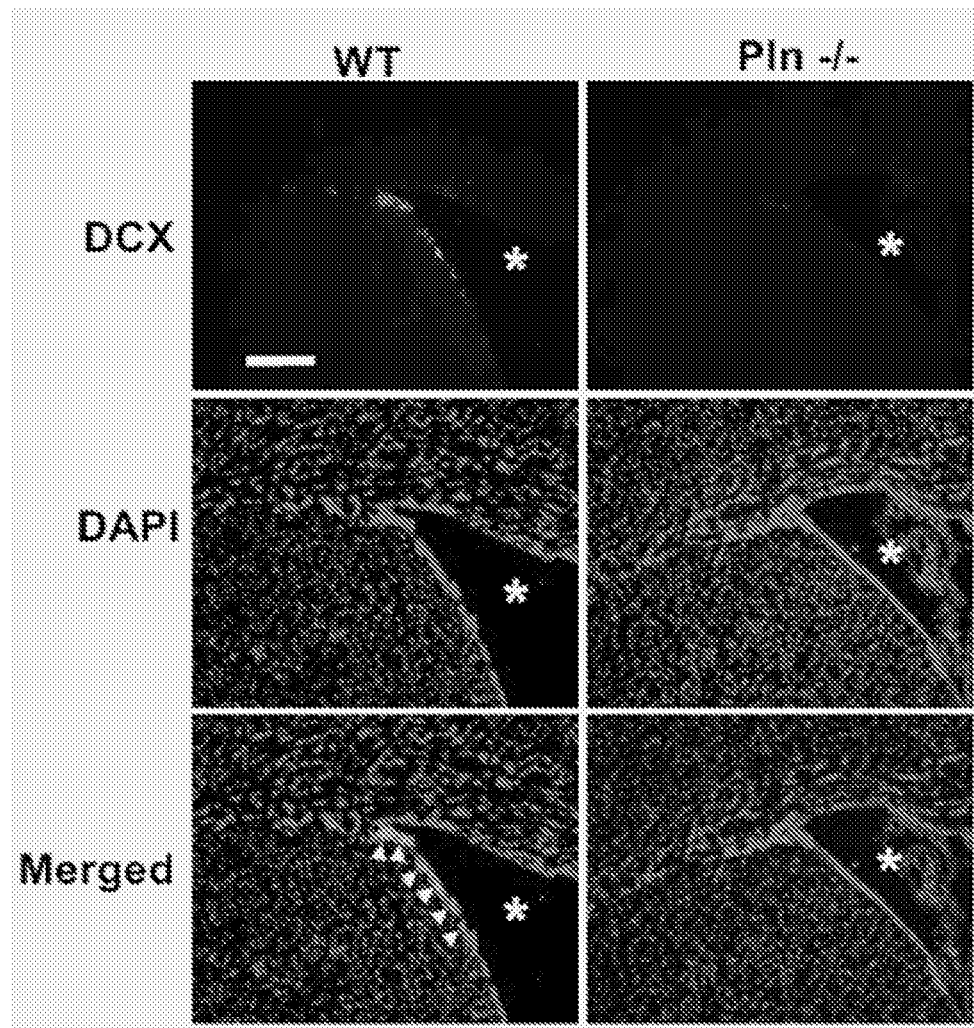
FIGS. 2A and 2B illustrate decreased neurogenesis in perlecan-deficient mice.
Figure 2B:
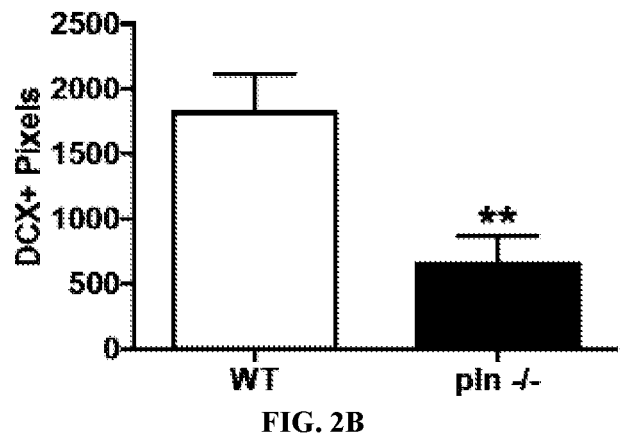
Figure 3A:
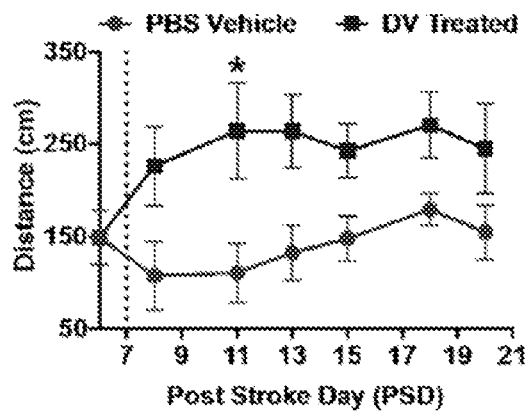
FIGS. 3A-3E illustrate that domain V (DV) improves sensorimotor function and nuclear histology in the stroke area.
Figure 3B:
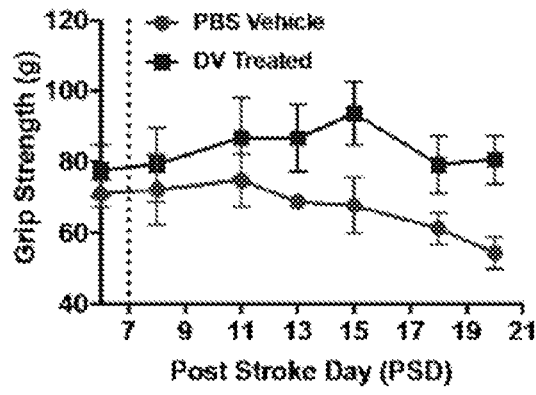

The rotor rod and grip strength behavioral tasks were used throughout the 3-week study to investigate the potential functional benefit of delayed DV administration. Prior to administration of DV on PSD7, there was no significant difference between the groups by posthoc analysis (stroked animals were not randomized into different treatment groups until PSD7). DV-treated mice showed a significant improvement overall (Two-Way RM ANOVA p<0.0001) on the rotor rod task compared to the PBS treated controls, particularly on PSD 11 (p<0.05; 263.8±52.5 vs. 110.7±31.5 cm, respectively), as shown in FIG. 3A. Mice treated with DV also performed significantly (p<0.001) better overall than the PBS treated control mice (FIG. 3B) in the grip strength test, indicating a marked functional improvement in the stroke affected forelimb following DV administration.

Figure 3C:
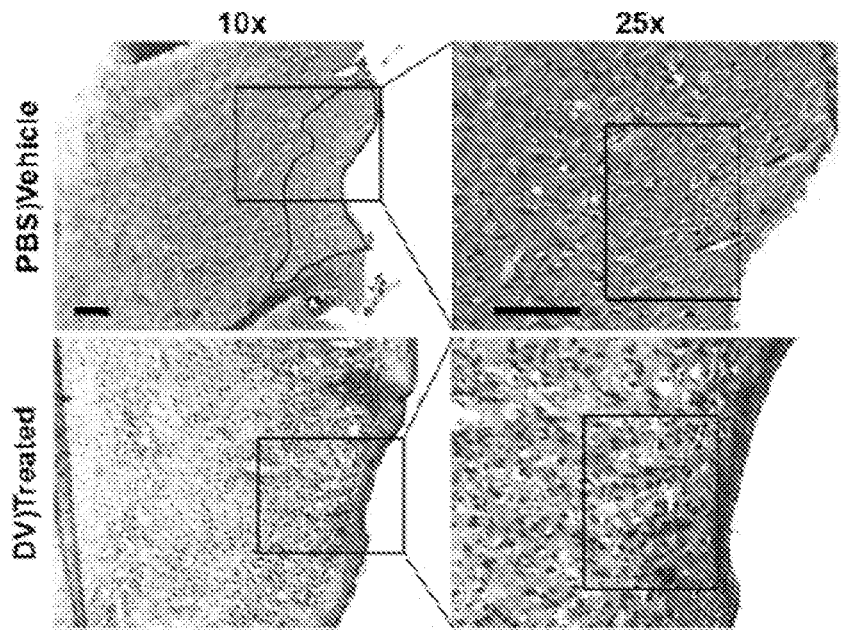
Figure 3D:
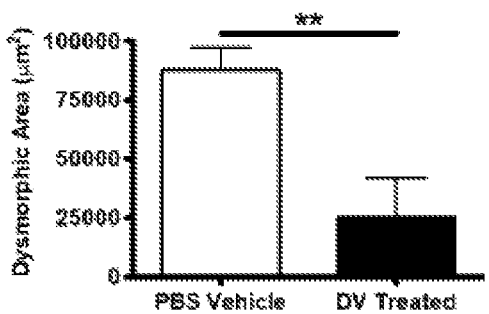
Figure 3E:
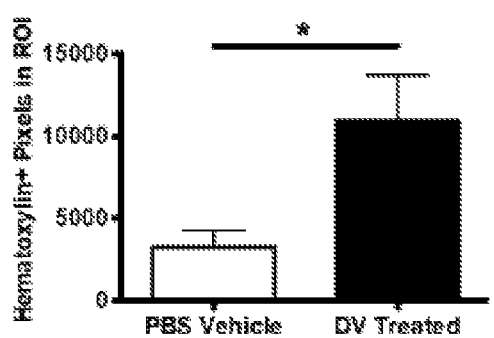

The extent of histological damage in the ipsilateral (stroke affected) cortex was also assessed to determine if delayed DV treatment could influence brain tissue health. DV treatment reduced (p<0.05) the size of hematoxylin and eosin (H&E)-stained dysmorphic areas (Defined by cellular loss/decreased cell and tissue density, smaller, irregular shaped nuclei or irregular tissue patterning from surrounding areas, FIG. 3C, D) compared to PBS treated stroked controls (25.32±16.4 vs. 87.56±9.5 mm$^2$, respectively) within regions of the cortex known to be consistently affected by this CCA/distal MCAo model. Of note, several of the DV treated animals did not have any detectable dysmorphic areas and no indication of contralateral injury was detected in any of the stroked mice (data not shown). Furthermore, DV treatment increased (p<0.01) the amount of hematoxylin positive pixels, used as an indicator of nuclei density, in similarly located equal-area regions of interest (ROI) within those dysmorphic areas compared to PBS treated controls (10960±2766 vs. 3245±1034 pixels/ROI; FIG. 3E).

TABLE 1

Descriptive data for human ischemic stroke patients for Domain V histological stains.

| Patient ID | Sex | Age | Stroke Onset to Death (Days) | Clinical Diagnoois |
|---|---|---|---|---|
| Control 1 | M | 78 | N/A | congestive heart failure |
| Control 2 | M | 41 | N/A | idiopathic pulmonary hypertension |
| 1 | M | 71 | 1 | basilar artery occlusion |
| 2 | F | 68 | 2 | systemic emboli/paroxysmal atrial fibrillation |
| 3 | M | 62 | 6 | old myocardial infarction/coronary artery bypass graft/bladder cancer/suspect adrenal tumor |
| 4 | F | 77 | 7 | heart failure/pneumonia |
| 5 | F | 89 | 7-8 | right internal carotid artery occlusion/suspect cardio embolic stroke |
| 6 | M | 78 | 21 | deep venous thrombosis/bilateral internal carotid artery occlusion/abdominal aortic aneurysm |
| 7 | F | 93 | 30 | MSRA-pneumonia |
| 8 | M | 56 | 90 | myocardial infarction/disseminated intravascular coagulation/suspect lung cancer/gastrointestinal bleeding |

Example 2: DV Increases Neurogenesis Following Experimental Stroke

Figure 4A:
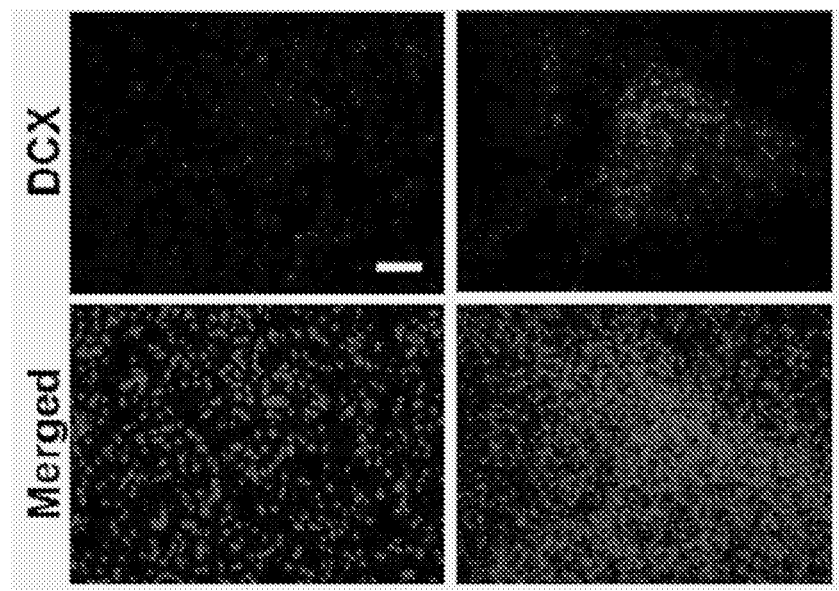
FIGS. 4A-4D illustrate that domain V (DV) increases neurogenesis in the stroke area.
Figure 4B:
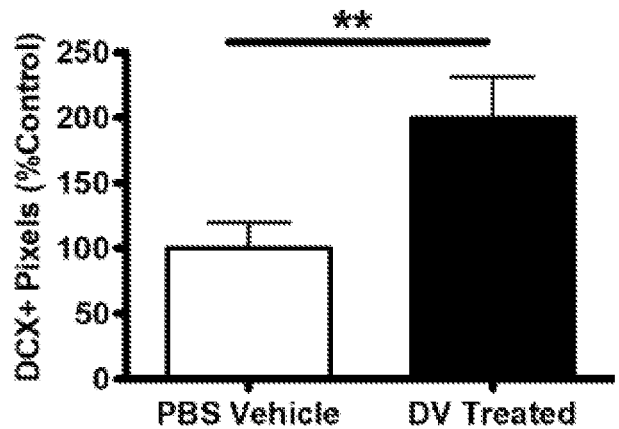

As 7-day delayed DV treatment increases cellularity in stroke-affected (i.e. core and peri-infarct) regions on PSD 21, it was investigated whether this could be the result of increasing neurogenesis, a mechanism of neurorepair. DCX immunofluorescence on coronal brain sections from animals that underwent transient MCAo injury with DV treatment starting on PSD 7 showed a significant (p<0.01) increase in DCX staining in the stroke-affected region on PSD 21 compared to PBS treated control mice (199.6±31.4% vs. 100.0±19.9%, respectively; FIG. 4A-B).

Because stroke therapeutic experimentation can be model and age specific, and post-stroke neurogenesis is known to be diminished with age, a second, mechanistically distinct, experimental stroke model in aged (24-month-old) mice was used to confirm and expand the findings that DV increases post-stroke neurogenesis. Permanent photothrombotic stroke was performed in aged mice followed by initiation of DV treatment 6 hours later. This 6-hour time point was chosen as this is when maximal DCX expression was seen in this focal model of stroke. The histological and behavioral results for these studies, in which DV was neuroprotective and promoted functional recovery to PSD 7, have previously been published[8]. As in the transient MCAo studies in young mice, DV treated aged mice had significantly higher DCX immunoreactivity in the area of the SVZ ipsilateral to the stroke infarct on PSD 7 (363.76±78.21%) compared to the PBS vehicle control (set to 100±19.48%; FIGS. 10A & 10B). At this earlier sacrifice time point, PSD7 versus PSD21, with less time to migrate away from the SVZ, as well as considering the advanced age of these mice, the majority of DCX positive cells were perhaps unsurprisingly identified in, and emerging from the SVZ rather than near the infarct region itself. Collectively, however, despite the distinct stroke model, the age of the mice, and the relatively shorter outcome measure, DV treatment still appeared to increase mobilization of immature neurons in the stroke affected brain.

Figure 4C:
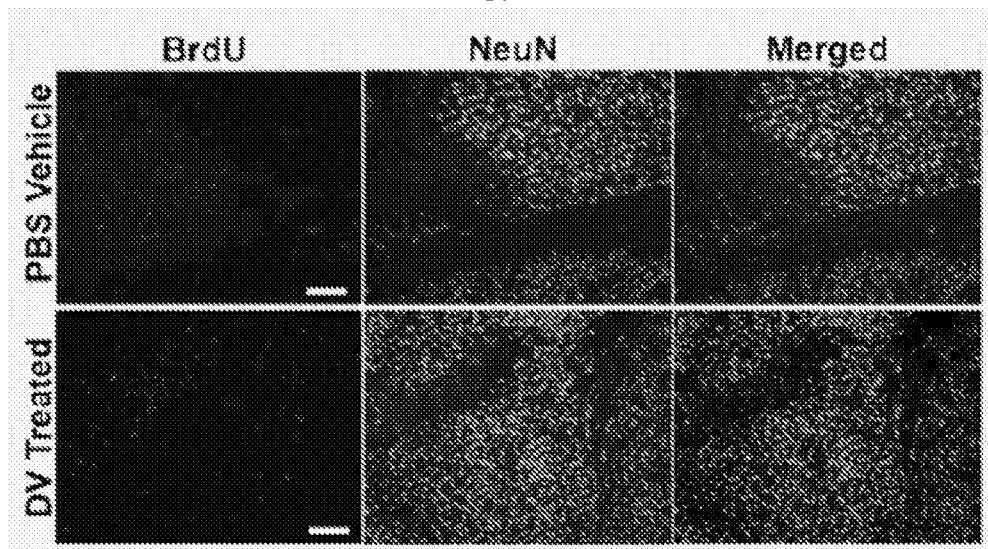
Figure 4D:
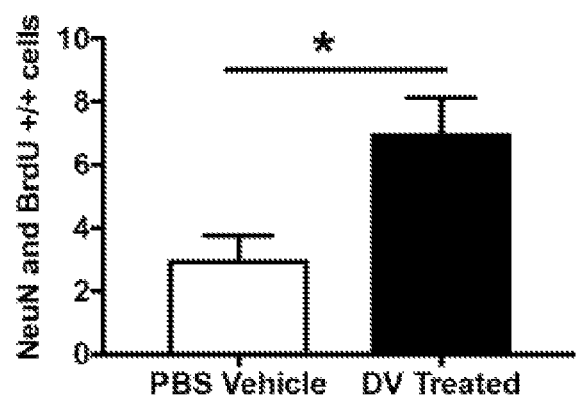

Studies were also conducted to determine whether increased DCX positive cells associated with DV treatment would translate into an increase in new (i.e. generated after stroke) mature neurons in the stroke damaged area following CCA/MCAo. Therefore, co-immunofluorescence was performed with NeuN, a pan-neuronal marker, and BrdU (a cell proliferation marker injected into the mice daily from PSD 7-13 (to label cells dividing after the first DV treatment) and again on PSD 20 and 21 (to label cells continuing to divide during the last 48 hours prior to the end of the study, see FIG. 9A); any cell that is positive for both markers is indicative of a mature neuron that was born from PSD 7 onwards. DV treated mice had significantly (p=0.0151) higher NeuN- and BrdU-positive co-immunoreactivity in the stroke damaged area (7±1.13 vs. 3±0.77 cells/ROI, respectively) on PSD 21 compared to PBS treated controls (FIGS. 4C & 4D).

Figure 5A:
FIGS. 5A-5G illustrate that delayed domain V restores excitatory synaptic drive to neocortical layer 2/3 pyramidal cells (L2/3PCs) 21 days following transient CCA/MCAo stroke injury.

Example 3: DV Restores Peri-Infarct Excitatory Synaptic Drive to Neocortical Layer 2/3 Pyramidal Cells Because DV enhanced post-stroke neurogenesis and new mature neurons, studies were also performed to test whether delayed DV treatment affected neocortical excitability after stroke. Neocortical layer 2/3 pyramidal cells (L2/3PCs) were selected for analysis because of their importance as a predominant site of synaptic integration within the neocortex[26]. Whole-cell patch clamp recordings were performed on L2/3PCs from mice after surgical sham or MCAo with control vehicle treatment (PBS Vehicle) or DV treatment (DV Treated; FIG. 5A). As a control measure, no group differences were detected for estimated locations of recorded L2/3PCs based on their relative distance to the most dorsal aspect of the slice and relative to the most dorsal-lateral aspect of the macroscopic lesion in injured animals (see Methods; Table 2). Additionally, the majority of intrinsic membrane properties of L2/3PCs were not significantly affected by stroke injury+PBS vehicle or stroke injury+DV treatment (Table 2). Membrane potentials were significantly more polarized in L2/3PCs from stroke injured mice (Vehicle: −58.4±2.0 mV, p=0.021; DV: −56.8±2.2 mV, p=0.0098) in comparison to L2/3PCs from sham injured mice (−67.2±2.5 mV, 1-Way ANOVA, F(2,31)=6.01, p=0.0062).

TABLE 2

Location, intrinsic and excitatory synaptic properties of neocortical layer 2/3 pyramidal cells (L2/3PCs) ex vivo. Dorsal-medial aspect of slice and dorsal aspect of lesion are locations of recorded L2/3PCs relative to these two landmarks (see Methods).

| | Experimental Group | | | |
|---|---|---|---|---|
| | Sham-injury | Injury + PBS | Injury + DV PBS | Statistical Test |
| Dorsal-medial aspect of slice (μm) | 2241.5 ± 174.8 | 2116.6 ± 183.9 | 2137.0 ± 264.7 | F(2, 31) = 0.11 p = 0.90 |
| Dorsal-lateral aspect of lesion (μm) | — | 1098.2 ± 138.6 | 1049.4 ± 230.6 | T(21) = 0.19, p = 0.85 |
| Input Resistance (MΩ) | 256.8 ± 48.1 | 246.9 ± 48.9 | 323.4 ± 54.5 | F(2, 31) = 0.65, p = 0.53 |
| AP Threshold (mV) | −33.7 ± 0.9 | −34.0 ± 1.2 | −32.8 ± 1.4 | F(2, 31) = 0.24, p = 0.78 |
| sEPSC Rise (ms) | 2.2 ± 0.06 | 2.1 ± 0.18 | 2.4 ± 0.13 | F(2, 30) = 0.69, p = 0.51 |
| sEPSC Decay (ms) | 3.1 ± 2.0 | 3.2 ± 0.32 | 3.7 ± 0.29 | F(2, 30) = 1.23, p = 0.31 |
| mEPSC Rise (ms) | 2.4 ± 0.22 | 2.0 ± 0.20 | 2.3 ± 0.10 | F(2, 21 = 1.39, p = 0.27 |
| mEPSC Decay (ms) | 3.4 ± 0.46 | 2.9 ± 0.3 | 3.4 ± 0.37 | F(2, 21) = 0.44, p = 0.65 |

Injury = tandem ipsilateral common carotid artery and distal middle cerebral artery occlusion stroke injury.
AP Threshold = action potential threshold.
sEPSCs = spontaneous excitatory post-synaptic currents.
mEPSCs = miniature excitatory post-synaptic currents.
P values were assessed by 1-Way ANOVA or Student's T test.
Data represent mean ± SEM.

Figure 5B:
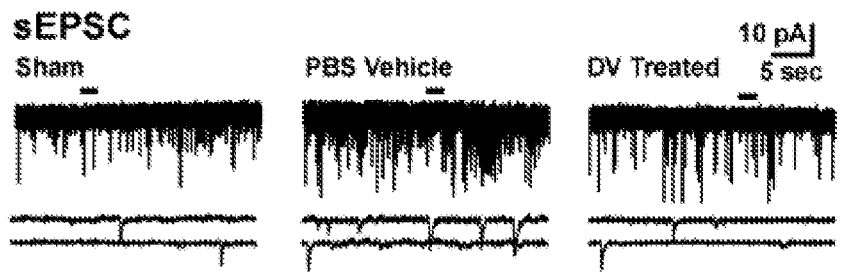
Figure 5C:
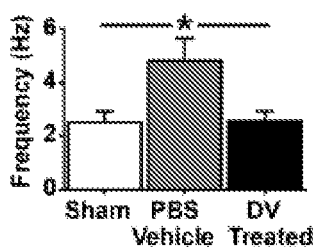
Figure 5D:
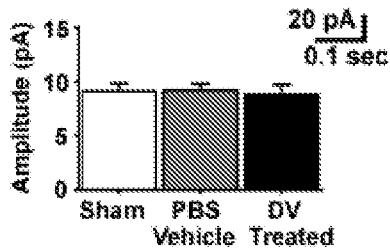

In addition to intrinsic properties, excitatory synaptic drive to neocortical L2/3PCs were also examined across the same experimental conditions. The frequency of spontaneous excitatory post-synaptic currents (sEPSCs) was significantly elevated in the PBS Vehicle-treated stroked animals (4.8±0.8 Hz, p=0.043) relative to sham controls (2.5±0.4 Hz, 1-Way ANOVA, F(2,30)=4.40, p=0.021; FIG. 5B,C). This effect of stroke injury on sEPSC frequency was reversed in the presence of DV treatment (2.6±0.4 Hz) when compared to stroke PBS Vehicle controls (p=0.048) and did not differ from sham controls (p>0.99). No significant changes were detected in sEPSC amplitude (F(2,30)=0.08, p=0.93), rise time or decay time between these treatment groups (FIGS. 5B & 5D; Table 2).

Figure 5E:
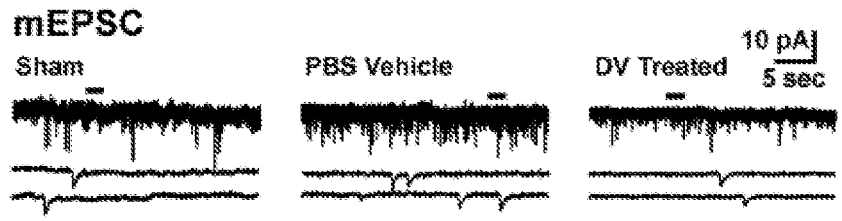
Figure 5F:
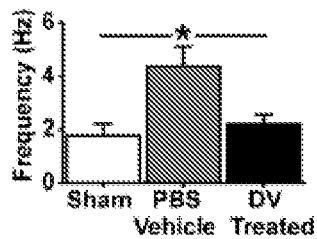
Figure 5G:
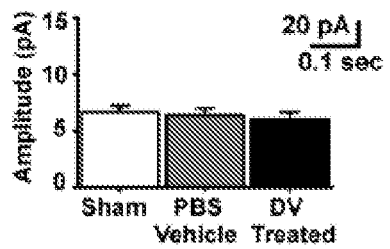

To better understand these changes in excitatory synaptic drive, these signals were measured in the presence of the voltage-gated sodium channel blocker tetrodotoxin (1 μM) in order to examine action-potential independent miniature excitatory post-synaptic currents (mEPSCs). mEPSCs provide a measure of the signaling properties of axonal terminals that directly innervate the recorded neuron. As with sEPSCs, the frequency of mEPSCs was significantly increased in cells from PBS Vehicle-treated stroked (4.4±0.7 Hz, p=0.0080) relative to sham controls (1.8±0.4 Hz) (1-Way ANOVA, F(2,21)=6.52, p=0.0063; FIG. 5E,F). DV treatment normalized mEPSC frequency in injured animals (mean: 2.2±0.4 Hz) when compared to stroke PBS Vehicle controls (p=0.034) with mEPSC frequencies not significantly different to sham control levels (p=0.86). No significant changes were detected in mEPSC amplitude (F(2,21)=0.29, p>0.75), rise time and decay time between these experimental groups (FIG. 5E,G; Table 2). Together, these data are consistent with DV exhibiting a restorative effect on synaptic plasticity; this provided a guide to subsequently examine the effects of DV signaling on neuronal proliferation, migration, differentiation and outgrowth.

Example 4: DV Increases Neural Precursor Cell Proliferation In Vitro

DV's neurogenic effects were investigated in vitro using cultured neural precursor cells (NPCs) isolated from brain neurogenic zones. Neurospheres undergo cell proliferation and sphere expansion while maintaining their undifferentiated state in suspension with mitogens such as epidermal growth factor (EGF)[27,28].

Figure 6A:
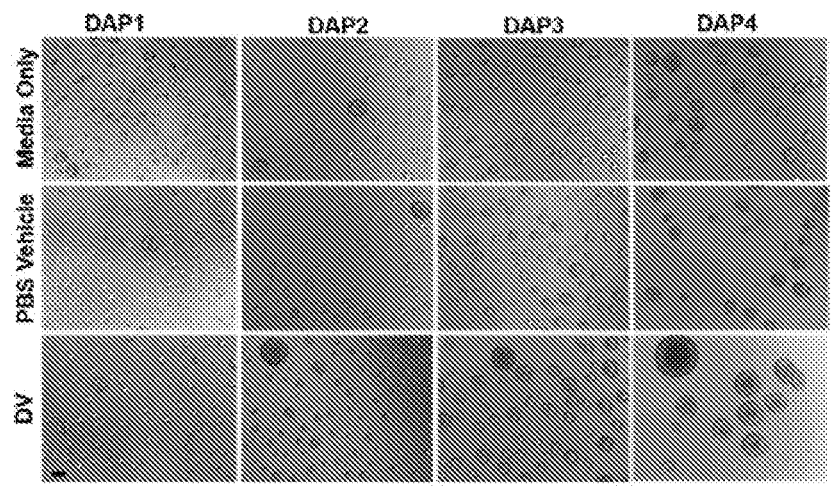
FIGS. 6A-6F illustrate that domain V increases neurosphere expansion, proliferation, and increases migration via an α2β1 integrin-dependent mechanism.
Figure 6B:
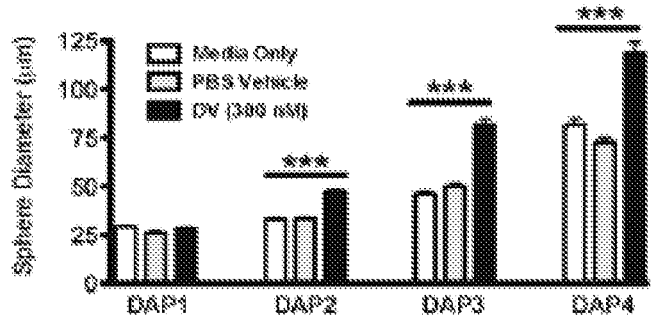

Studies were conducted to examine whether DV could increase neurosphere expansion under proliferative conditions by imaging the formation (from NPCs) and diameter expansion of neurospheres over 4 days (FIG. 6A). DV treatment increased (p<0.001) neurosphere diameter beginning on the day after plating (DAP) 2 and persistently through DAP4 (47.2±0.9 μm on DAP2, 82.2±2.5 μm on DAP3, 118.6±5.7 on DAP4) compared to media only controls (33.3±0.6 μm on DAP2, 46.3±1.1 μm on DAP3, 81.9±3.2 μm on DAP4; FIG. 6B). PBS vehicle controls were not different from the media only condition.

Figure 6C:
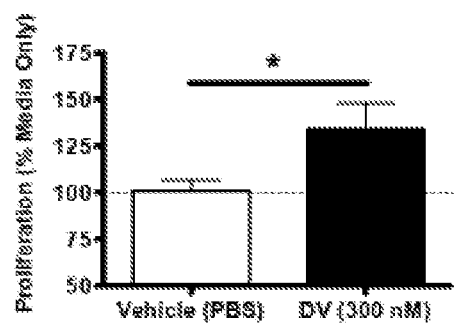

Given these results, studies were conducted to determine whether the increase in neurosphere size with DV treatment was predominantly the result of increased cell proliferation rather than solely caused by other effects that could potentially influence the appearance of neurosphere size, such as cell adhesiveness. To that end, cell counts were performed at the termination of neurosphere expansion experiments and found that DV increased (p<0.005) viable cell numbers compared to the PBS vehicle control (media only condition set to 100%, compared to 179.2±16.21% and 115.9±1.61%, respectively for DV and PBS vehicle control; FIG. 11A). DV's proliferation effects were further confirmed with MTS proliferation assays where DV increased NPC proliferation on DAP2 compared to PBS vehicle (media only condition set to 100%, compared to 134.2±13.57% and 101.1±5.50%, respectively for DV and PBS vehicle control; FIG. 6C).

Finally, to further verify DV effects on NPC proliferation, BrdU incorporation assays were performed. Neurosphere-dissociated cells were plated as in expansion assays, but adherent on 100 µg/mL Poly-d-Lysine (PDL). Here, DV increased (p<0.005) the percentage of BrdU immunopositive cells, with total cell number determined by DAPI nuclear counterstain, compared to the PBS vehicle condition, neither of which differed from the media only condition (Media only condition set to 100%, 172.3±17.80% DV, 95.68±8.87% PBS vehicle; (FIG. 11B)). Collectively, DV enhanced the proliferation of NPCs by suspended neurosphere expansion, viable cell counts, MTS assays, and adherent BrdU incorporation assays thereby warranting further mechanistic analysis.

Example 5: The DV α2β1 Integrin Receptor and Neurogenesis

Since it was previously demonstrated that α2β1 integrin is a DV receptor in cultured human and mouse fetal cortical neurons[29,30], and as the β1 integrin family (made up of at least 10 different alpha subunit combinations with β1) has been implicated in neurogenesis[31-35], it was contemplated that α2β1 integrin could play a previously unrecognized role in post-stroke neurogenesis and be a key receptor for DV's neurogenic effects. To test this hypothesis, the manner in which DV and α2 interact was tested in an in vitro model of neurogenesis using neurospheres. Importantly, because α2 integrin aids in cell adhesion, investigating its role in the proliferative phase of neurosphere neurogenesis in vitro (a cell-adhesion dependent assay) was impractical. Therefore, the potential role of α2 integrin in neuronal migration, differentiation, and neurite extension, and whether this modulated DV neurogenic effects, was investigated.

Example 6: DV Increases Neurosphere Migration Through an α2β1-Integrin Dependent Mechanism Studies were conducted to determine whether DV could increase migration of NPCs out of neurospheres, which occurs in a "spokes of a wheel pattern" when the neurospheres adhere to a substrate without mitogens[36]. To that end, whole neurospheres were plated on PDL in proliferation media without EGF, thereby reducing the NPCs proliferative drive. The spheres settled, attached to the substrate, and began extending radially into a cluster of adherent cells that were imaged at multiple hour time points after plating (also notably prior to when DV effects were seen on proliferation at DAP2; FIG. 6A) (HAP; FIG. 11C). Although cells were occasionally observed migrating out of the cluster, on this substrate the vast majority of cells migrated slowly from the adherent sphere forming a larger cell cluster. DV treatment significantly (p<0.001) increased the diameter of adherent cell clusters compared to the media only control at 24 HAP (2.2±0.1 and 1.8±0.1 normalized cluster diameter µm, respectively; FIG. 11D). At time points later than 24 HAP, cell clusters had extended out of the microscope image field making us unable to quantify cluster diameter past 24 HAP.

Although these assays assessed cell migration out of neurospheres, given the 24 HAP time taken for differences to emerge between groups on the PDL substrate, it is possible that DV effects on neural precursor cell proliferation could have partially contributed to the differences in size of cell clusters. Therefore, whole neurospheres were next plated on PDL and laminin (15 µg/mL) to facilitate cell migration out of neurospheres. On PDL/laminin, the spheres settled and attached to the substrate and extensively migrated by 6 HAP (FIG. 11E). DV treatment significantly (p<0.001) increased the distance that cells migrated out of the sphere (155.9±4.3%) compared to the PBS vehicle (94.6±2.3%) condition (media only condition set to 100%; FIG. 11F).

Figure 6D:
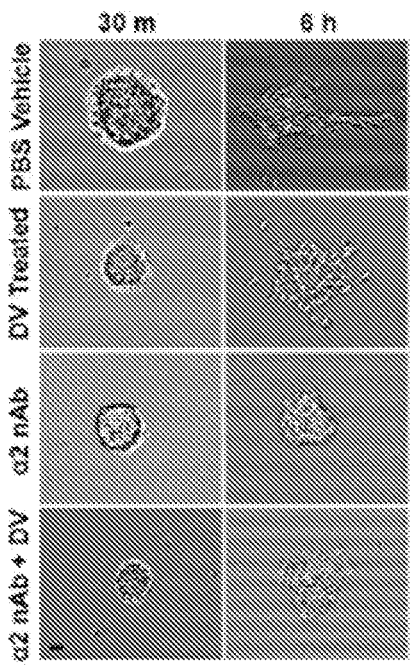
Figure 6E:
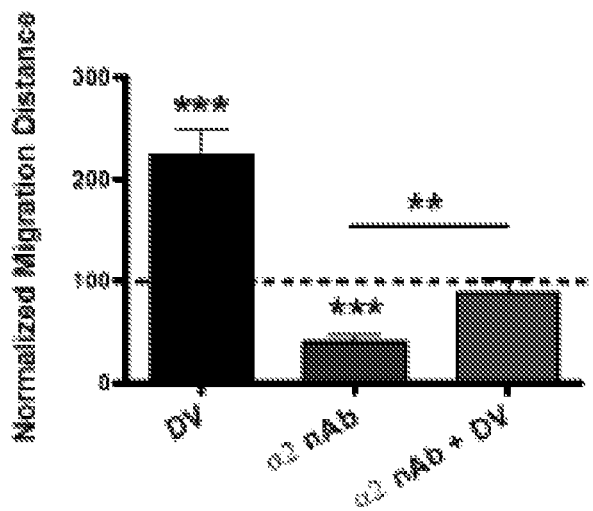
Figure 6F:
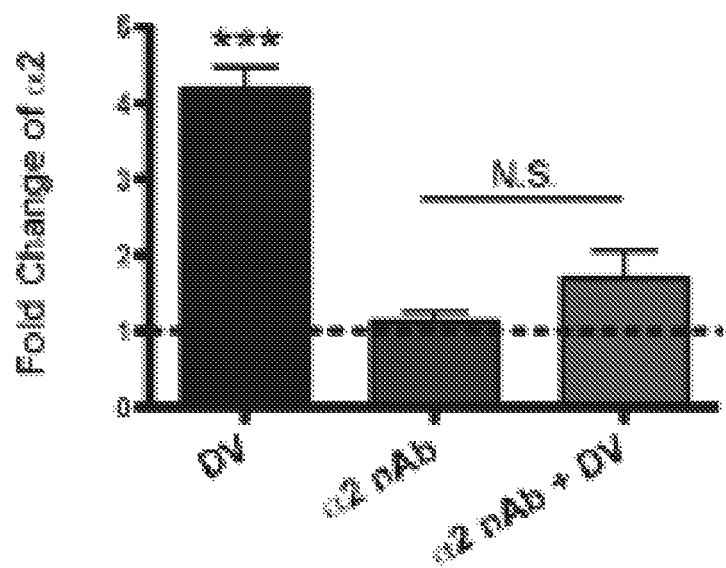

Next, studies were conducted to determine whether α2β1 integrin had an effect on endogenous NPC migration out of neurospheres. Under α2 neutralizing antibody (nAb) conditions[29], NPC migration out of neurospheres was significantly (p<0.001) decreased (40.0±7.4% compared to PBS vehicle set to 100%; FIG. 6D-E). Furthermore, DV treatment was unable to overcome the anti-migratory effects of the α2 nAb (FIG. 6D-E). The significance of α2β1 integrin to DV's pro-migratory effects is further supported by the finding that DV significantly (p<0.001) increased α2 gene expression (4.2±0.3 fold compared to PBS vehicle; FIG. 6F). Moreover, α2 nAb diminished DV's effects on α2 transcription (α2 nAb: 1.1±0.1 fold, α2 nAb+DV: 1.7±0.4 fold; FIG. 6F), suggesting a positive feedback loop between DV, α2β1 integrin signaling, and α2β1 integrin transcription in NPCs. Taken together, these results suggest that α2β1 integrin plays a significant role in NPC migration and that DV increases the migration of NPCs out of neurospheres in an α2β1-integrin mediated fashion.

Figure 7A:
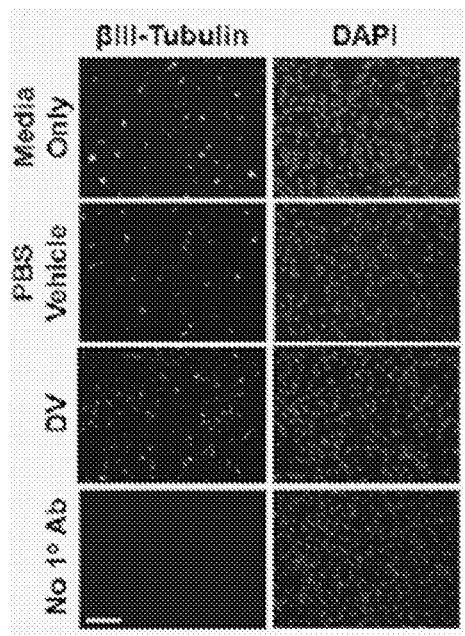
FIGS. 7A-7H illustrate that domain V increases neuronal differentiation of neurosphere-dissociated cells and neurite extension and outgrowth of primary cortical neurons partly through an α2β1 dependent mechanism.
Figure 7B:
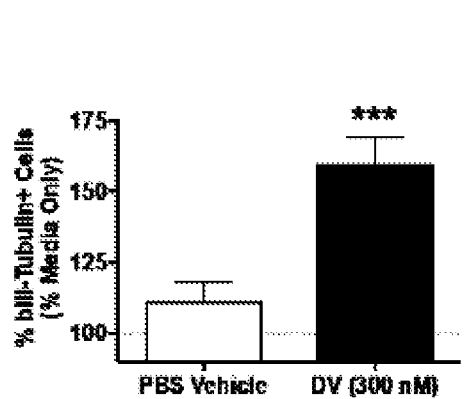
Figure 7C:
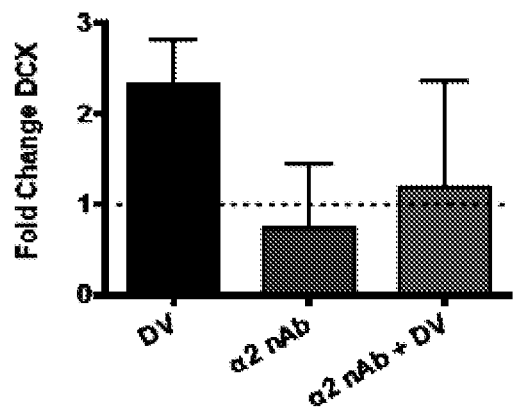

Example 7: DV Increases Neuronal Differentiation of Neurosphere-Dissociated Cells in an α2β1-Integrin Mediated Fashion Studies were next conducted to determine whether DV-induced neuronal differentiation of neurosphere-dissociated cells into neurons when they were plated on a substrate in differentiation media without mitogens[27,28]. On DAP6, DV significantly increased the percent of neurosphere-dissociated cells that differentiated into βIII-Tubulin positive neurons (160.2±8.9%) compared to PBS vehicle control (111.4±6.8%, Media only condition set to 100%; FIG. 7A-B). To determine if α2β1 is also involved in differentiation, neurosphere-dissociated cells were treated with the α2 nAb with or without DV. Quantitative PCR analysis showed that DV increased DCX expression 2.2 fold compared to PBS vehicle treated neurospheres (FIG. 7C). Treatment with α2 nAb decreased DCX gene expression compared to PBS vehicle treated cells, which could not be overcome by DV (α2 nAb: 0.7±0.4 fold and α2 nAb+DV: 0.4±0.4 fold). Taken together, these results demonstrate that DV increases differentiation of NPCs into neurons and that this process may depend, at least in part, on α2β1 integrin.

Figure 7D:
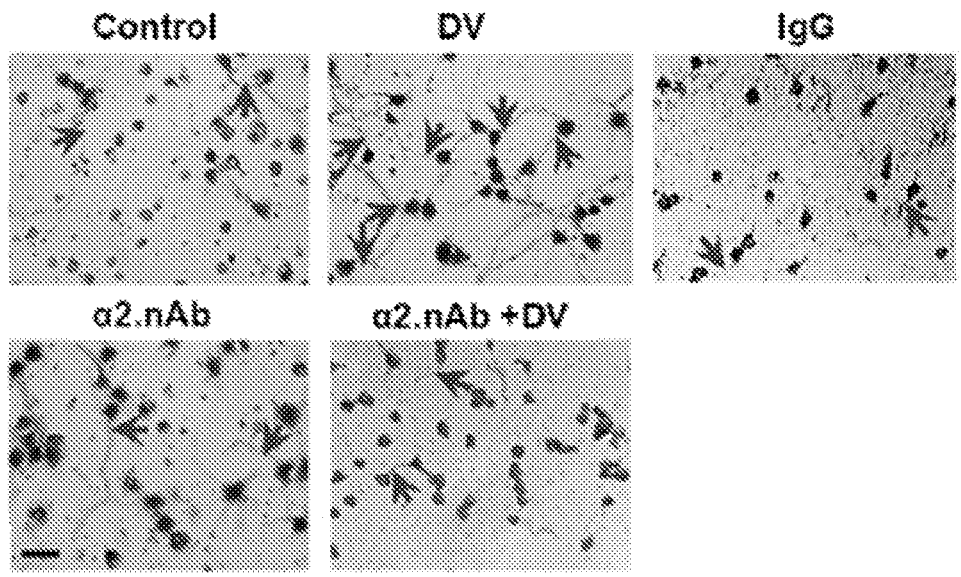
Figure 7E:
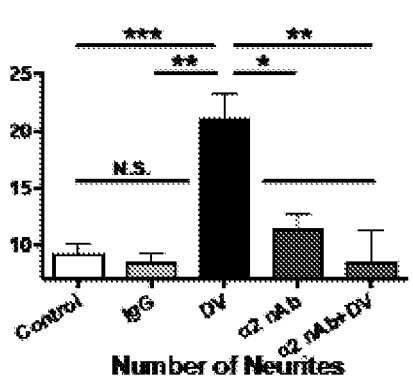
Figure 7F:
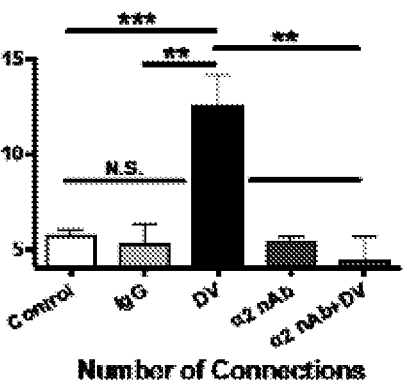
Figure 7G:
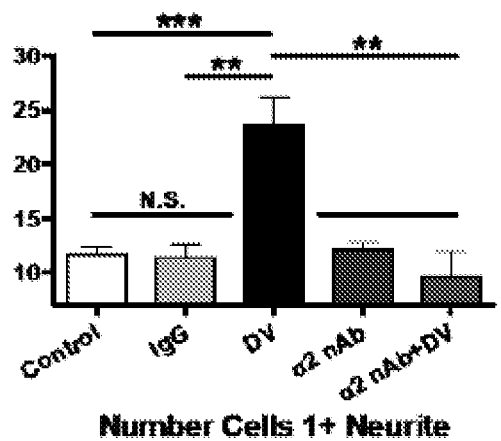

Example 8: DV Increases Fetal Cortical Neuron Neurite Extension and Connectivity in an α2β1-Integrin Dependent Manner Neurite extension is an important step following neuronal genesis, migration, and differentiation as it is necessary for ultimate synaptic connectivity. It was conceived that DV could play a role in this process in an α2β1-integrin dependent manner given that: 1) full length bovine perlecan has been demonstrated to promote neural stem/neural precursor cell neuritogenesis in vitro[16], 2) the β1 integrin subunit of the heterodimeric DV integrin receptors α2β1 and α5β1 has repeatedly been implicated in neurite extension[24,25,27], 3) α2β1 has also been associated with neurite extension in retinal ganglion cells[28], and 4) DV has been shown to act through the α2 integrin in various cell types including astrocytes, fetal cortical neurons, and umbilical vein and dermal endothelial cells as previously mentioned[36-38]. To that end, DV's effects on neurite extension and connection was assessed using primary mouse E16 fetal cortical neurons (FCN). FCN were used to more specifically examine DV effects on neurons compared to the mixed population of neurosphere-dissociated cells. It was observed that DV significantly enhanced neurite extension and connectivity after 4 hours (FIG. 7D). Indeed, DV increased the numbers of neurites, cells with 1 or more neurites, and cell-cell connections compared to the media only condition (values and statistics for neurite experiments are shown in Table 3 and graphed in FIG. 7E-G). As in the migration and differentiation studies, DV could not overcome the effects of an α2 nAb, although in these studies α2 nAb did not reduce these neurite measures below vehicle or IgG control levels (Table 3; FIG. 7D-G), suggesting the potential importance of α2β1 integrin specifically to DV neurite effects.

TABLE 3

Means of neurite extension and connectivity in mouse fetal cortical neurons in vitro. Descriptive statistics for FIG. 6D.

| | Mean | S.E.M. | One-Way ANOVA | Tukey's Post-hoc test [ ]: DV |
|---|---|---|---|---|
| Number of Neurites | | | | |
| Control | 9.332 | 0.81 | $F_{(4, 13)} = 11.58$ | ***$p < 0.001$ |
| IgG | 8.477 | 0.81 | ***$p = 0.0003$ | **$p < 0.01$ |
| DV | 21.16 | 2.174 | | |
| α2 nAb | 11.52 | 1.241 | | *$p < 0.05$ |
| α2 nAb + DV | 8.524 | 2.81 | | **$p < 0.01$ |
| Number of Cells 1 + Neurite | | | | |
| Control | 11.87 | 0.606 | $F_{(4, 13)} = 12.16$ | ***$p < 0.001$ |
| IgG | 11.55 | 1.119 | ***$p = 0.0002$ | **$p < 0.01$ |
| DV | 23.76 | 2.449 | | |
| α2 nAb | 12.36 | 0.519 | | **$p < 0.01$ |
| α2 nAb + DV | 9.857 | 2.143 | | **$p < 0.01$ |
| Number of Cell-Cell Connections | | | | |
| Control | 5.747 | 0.234 | $F_{(4, 13)} = 10.71$ | ***$p < 0.001$ |
| IgG | 5.31 | 1.024 | ***$p = 0.0005$ | **$p < 0.01$ |
| DV | 12.59 | 1.585 | | |
| α2 nAb | 5.474 | 0.141 | | **$p < 0.01$ |
| α2 nAb + DV | 4.405 | 1.262 | | **$p < 0.01$ |

Figure 7H:
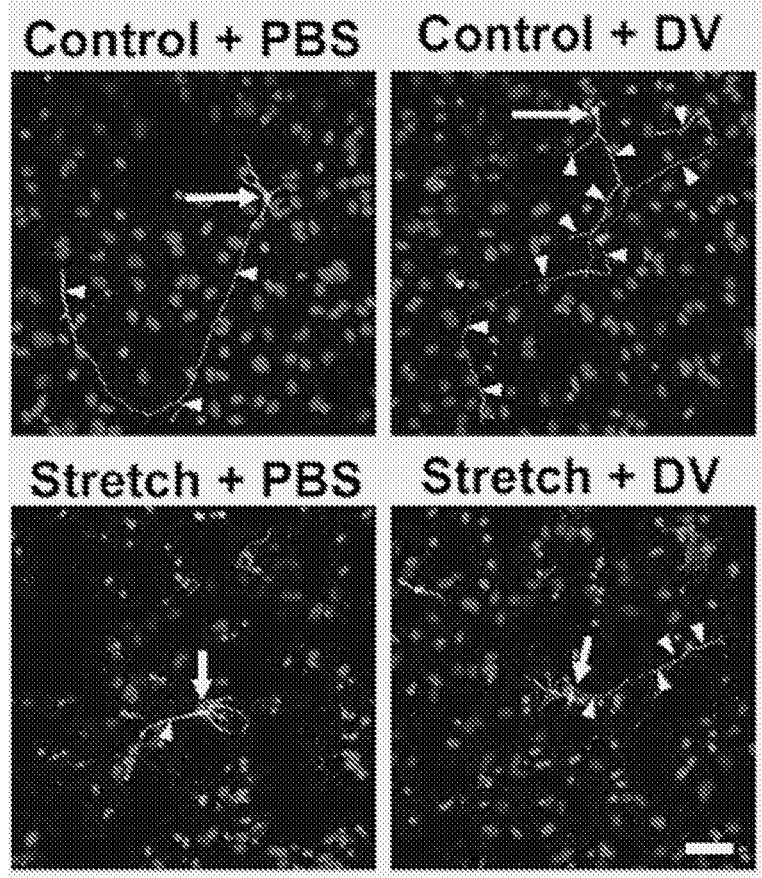

Example 9: DV Increases Cortical Neuron Neurite Extension in an In Vitro Reactive Gliosis Model To further test the functional effects of DV on neurite outgrowth, an in vitro model of reactive astrogliosis was used[39-41]. Mechanical stretch of cultured astrocytes has been shown to induce reactive gliosis[39-41]. As reactive gliosis occurs following stroke and traumatic injury, this co-culture stress model offers an excellent in vitro tool to assess neurite outgrowth[39,41]. Outgrowth of cortical neurons is impaired when cultured on stretched reactive astrocytes when compared to neurons cultured on non-stretched control astrocytes (FIG. 7H). Stretch resulted in a 35% decrease in neurite length compared to PBS treated non-stretched controls (control+PBS: 100±4.3 vs. stretch+PBS: 64.6±3.7%; FIG. 7I), showing the inhibitory effect of reactive gliosis (also present following stroke) on neurite extension. Treatment with DV (300 nM) resulted in a significant increase in neurite length in both non-stretched (control+PBS: 100±4.3 vs. control+DV: 114.8±4.6%, P<0.05) and stretched (stretch+PBS: 64.6±3.7 vs. stretch+DV: 76.8±3.9%, p<0.05) conditions. These results indicate that DV can facilitate neuronal sprouting of new connections in in vitro reactive gliosis, or scar-like, conditions.

Example 10: α2β1 Integrin Plays an Important Role in Post-Stroke Neurogenesis

Figure 8A:
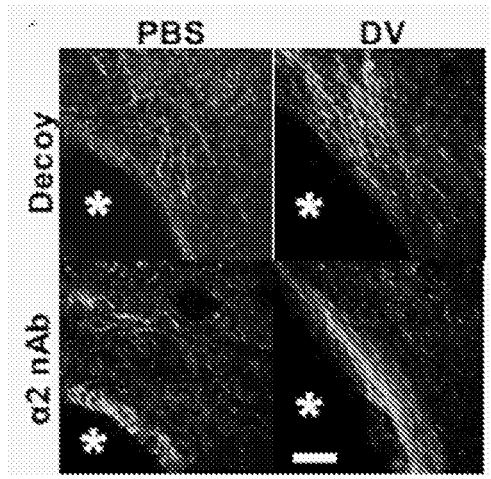
Figure 8B:
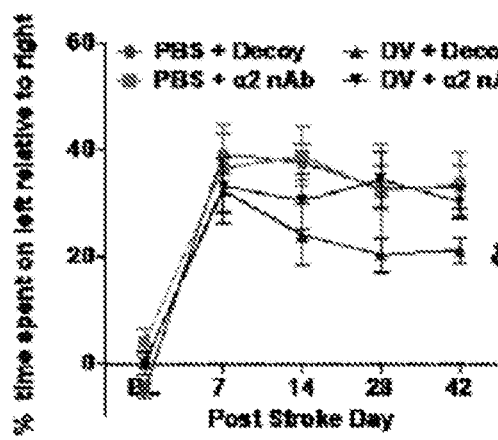
Figure 8C:
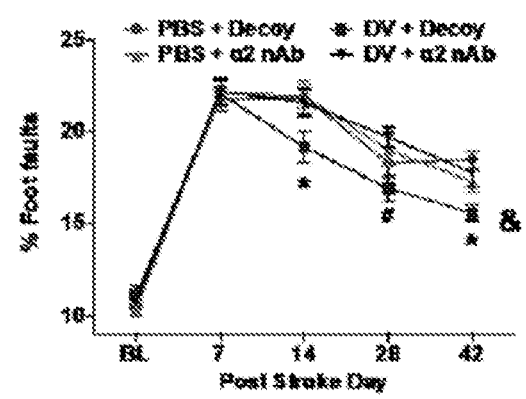
Figure 8D:
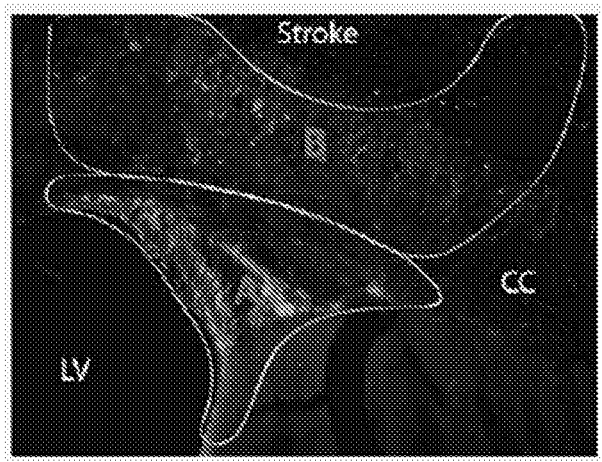

As the results with the α2 nAb suggest that α2β1 integrin plays a previously unrecognized role in neurogenic processes in vitro, studies were conducted to determine whether α2β1 integrin could also be important to DV's post-stroke neurogenic effects in vivo. First, DV or PBS vehicle was administered 6 hours after photothrombotic stroke in young C57Bl/6J mice and then α2β1 integrin was blocked with intrathecal treatment of the α2 nAb or IgG control (decoy) on PSD 3. As expected, WT mice treated with DV had a significant increase in DCX positive cells in the SVZ area lining the lateral ventricle of the stroked ipsilateral hemisphere on PSD 42 (FIG. 8A) compared to PBS control animals. Next, α2 integrin's role in DV's effects on post-stroke functional outcome was examined. Following photothrombotic stroke, mice treated with DV had a significant (p<0.05) improvement in motor skills, as measured by grid walk, compared to those treated with vehicle, within 2 weeks (18.9±1.0 vs. 21.9±0.9 foot faults, respectively) and at 6 weeks (15.5±0.5 vs. 18.5±0.5, foot faults, respectively) post-stroke (FIG. 8C). A significant difference (p<0.05) was also observed between DV treated and DV+α2 nAb treated mice at 42 days (17.0±0.9 vs. 19.7±0.6, foot faults, respectively) post-stroke. Importantly, no difference was observed between mice administered DV+α2 nAb and those given vehicle, suggesting that DV works predominantly through an α2 integrin-mediated mechanism. These effects were also observed in the cylinder test, with the DV treated group significantly (p<0.05) different than the vehicle treated group across time (FIG. 8B). Finally, α2 nAb by itself did not significantly affect functional outcomes after stroke as compared to vehicle treatment (FIG. 8B-C).

α2 nAb treatment in stroked PBS-treated mice significantly decreased the number of DCX positive cells compared to the decoy treated stroked animals (30.8±4.5 vs. 63.4±6.8 cells, respectively) in the SVZ area lining the lateral ventricle including the bottom half of the corpus callosum on PSD 42 (Region A) (FIG. 8D, E). Furthermore, α2 nAb muted (72.2±13.3 cells) but did not entirely prevent DV's effect (100.0±13.4 cells) in Region A (FIG. 8D, E). Additionally, DV increased the number of DCX positive cells in the top half of the corpus callosum and the area surrounding the stroke cavity (Region B, 21.6±4.7 cells vs. 4.8±1.5 cells for decoy+PBS; FIG. 8D, F), and this was completely inhibited by the α2 nAb (α2 nAb by itself did not influence DCX positive cells in Region B; FIG. 8D, F).

Next, as electrophysiologic analysis demonstrated that delayed post-stroke DV treatment had a restorative effect on reactive synaptic plasticity after transient MCAo (FIG. 5), studies were conducted to determine whether DV might also affect dendrite density in peri-infarct regions after photothrombotic stroke (and whether this may also be α2β1 integrin dependent) via microtubule-associated protein (MAP)2 immunofluorescence. It was found that DV treatment increased (p<0.001) MAP2 immunofluorescence signal in four distinct peri-infarct regions, which was inhibited by α2 nAb (p<0.001, FIG. 8G, H). α2 nAb by itself had no effect of MAP2 immunofluorescence signal as compared to decoy treated stroked controls (FIG. 8G-H).

Figure 8I:
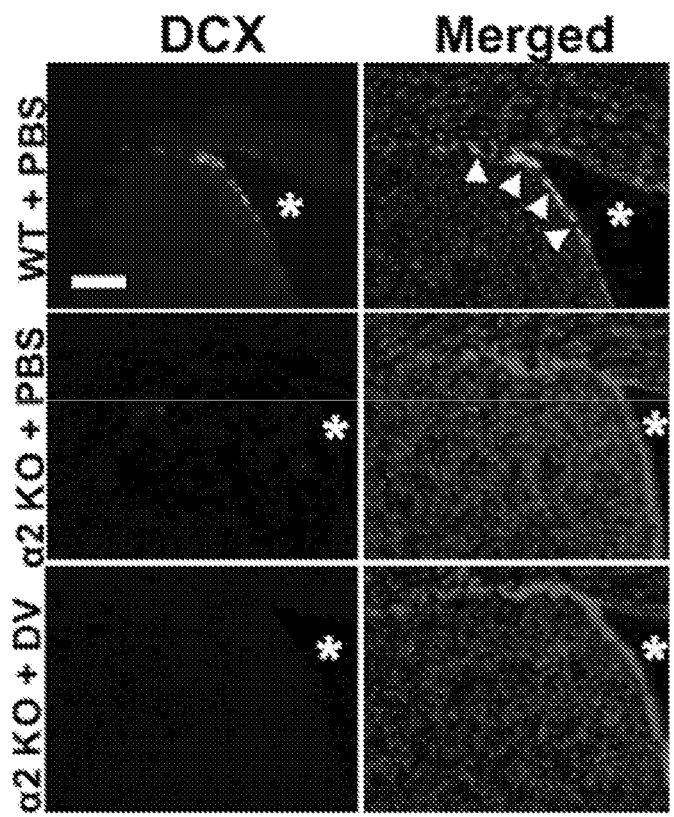
Figure 8J:
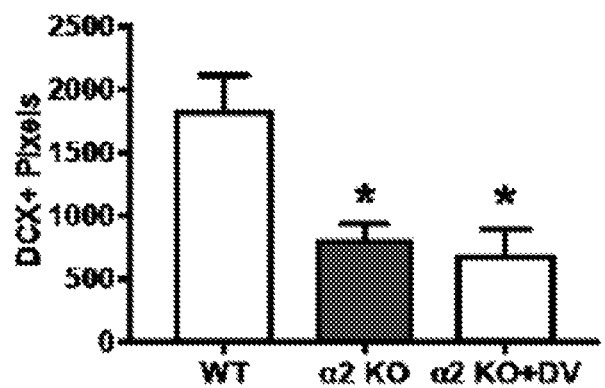

Finally, because the in vitro (FIGS. 6 & 7) and in vivo studies with α2 nAb suggested that α2β1 integrin by itself could play an important role in neurogenesis, post-stroke neurogenesis in α2 integrin null mice (α2 KO) was examined.[42] Importantly, α2 KO mice are phenotypically normal,[42] and analysis demonstrated no anatomic cerebrovascular abnormalities (FIG. 12). In seeming agreement with the α2 nAb studies, it was noted that α2 KO mice had significantly ($P<0.05$) less DCX immunoreactivity in the subventricular zone on PSD 14 than stroked WT controls (FIG. 8I, J). Furthermore, this post-stroke neurogenesis phenotype could not be rescued by administered DV (FIG. 8I, J), collectively further supporting the conclusion that α2β1 integrin plays an important role in DV neurogenic activity and suggests that α2β1 integrin itself plays an important role in post-stroke neurogenesis.

Examples 1-10: Discussion

In these Examples, studies were conducted to determine whether perlecan could play a role in post-stroke neurogenesis, whether perlecan DV (an 85-kDa portion of perlecan) treatment could stimulate post-stroke neurogenesis in WT mice and, if so, whether this effect might be associated with therapeutic (histological, electrophysiological and functional) benefit with a broad therapeutic window[19]. Potential DV neurogenic mechanisms of action were also investigated. These studies were predicated on previous studies that have implicated perlecan in developmental neurogenesis[14-16] as well as previous observations that perlecan-deficient mice experience larger ischemic infarcts and less reparative angiogenesis. Furthermore, acutely administered DV crosses the blood-brain barrier and is pro-angiogenic, neuroprotective, and restores motor function after experimental stroke in both young and aged mice and rats, and rescues the perlecan deficient mouse stroke phenotype[6,8]. It has also been demonstrated that DV exerts its neuroprotective and pro-angiogenic effects by: 1) interaction with the brain endothelial cell α5β1 integrin receptor, 2) subsequent activation of the ERK intracellular signaling pathway, 3) downstream release of VEGF[6,43], and ultimately decreased post-stroke neuronal apoptosis[6].

Figure 8K:
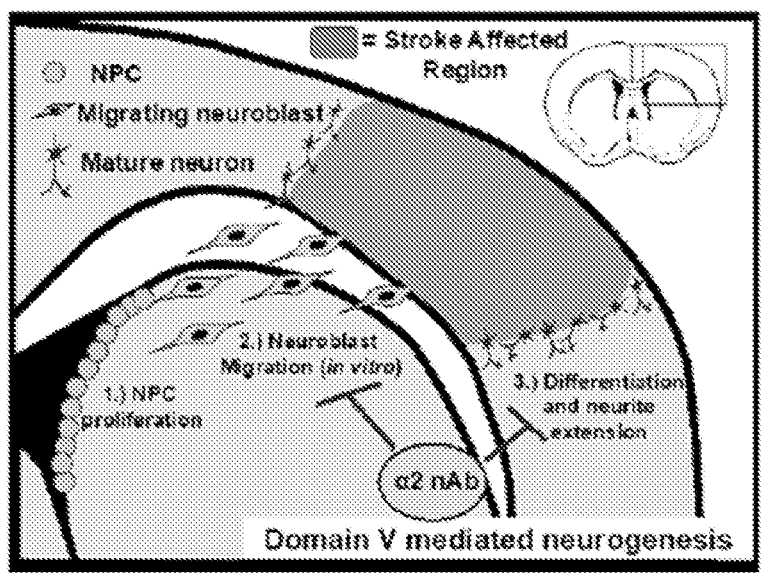

In these studies, the evaluation of post-stroke DV cellular and molecular therapeutic mechanisms of action has been dramatically expanded, thereby strengthening its translational and clinical relevance. It is shown that perlecan DV is upregulated chronically (out to 90 days) following human ischemic stroke, suggesting that this protein may play a functional role post-stroke and that it may be well-tolerated in stroke patients. Notably, perlecan deficiency in mice (90% reduction) results in significantly impaired post-stroke neurogenesis. This observation of a chronic impact of perlecan deficiency after stroke builds upon previous work demonstrating that perlecan processing plays an important role in the acute response to stroke[6]. Furthermore, when administered to stroked WT mice (in both young and aged mice in two distinct stroke models, MCAo and photothrombotic stroke), DV increases neurogenesis, the number of new neurons in stroke affected areas, and neurite density in the stroke affected cortex, and restores excitatory synaptic drive in these neurons. In addition, DV stimulates several aspects of neurogenesis (proliferation, migration, differentiation, and neurite extension) in vitro, at least partly via the α2β1 integrin. These results reinforce previous work[6] demonstrating that further augmenting elevated endogenous post-stroke DV levels with additional administered DV can provide benefit, perhaps best summed up as "if some (DV) is good, more is better". It was also demonstrated that DV therapy improved functional outcome for as long as 42 days in an α2β1 integrin dependent fashion, given that DV's therapeutic benefit was abrogated by an α2β1-neutralizing antibody or in α2 integrin KO mice (that also had deficient post-stroke neurogenesis). These results are summarized in FIG. 8K.

Importantly, in some of the in vivo experiments, DV treatment was delayed until PSD 7 to minimize the confounding impact of DV neuroprotective and pro-angiogenic effects, occurring when DV is administered within 24 hours after stroke, and focused on neurogenesis to examine a potentially larger therapeutic window for DV stroke treatment[6,8]. Furthermore, to ensure that any potential DV neurogenic effects were not unique or limited to a single stroke model, two models of experimental stroke were used, MCAo and photothrombosis. The MCAo model is mechanical and transient with a reperfusion component whereas the photothrombosis model is permanent and less invasive. Finally, young as well as aged mice were used since almost 90% of strokes occur after 65 years of age in humans[44] and the elderly have a reduced capacity to recover compared to younger stroke survivors[45]. In the photothrombotic stroke model, it was determined that early (6 hr) DV treatment increased the number of immature neurons in the SVZ and pen-infarct areas on PSD42 in young mice, and in the pen-infarct areas on PSD 7 in aged mice, while delayed (7 day) DV treatment in the transient MCAo stroke model increased the number of new neurons (DCX+ and BrdU+/NeuN+) within the stroke-affected area on PSD 21 in young mice. The ability of DV to increase neurogenesis in aged stroked mice is both clinically relevant and remarkable given that aged mice have a diminished neurogenic capacity[46]. Furthermore, the effectiveness of 7 day delayed DV treatment on increasing neurogenesis, enhancing survival and differentiation of neuroblasts into neurons, and improving motor function in stroked adult animals strongly supports the hypothesis that DV can enhance post-stroke repair mechanisms. Finally, relative differences in the timing of DV dosing between the two stroke models to affect DCX expression may be due to differences in how the stroke injury is induced and/or the rate at which the injury evolves (e.g. apparent peak infarct volume is achieved within 24 hours after photothrombosis, but takes 3 days in the MCAo model)[6,8].

Intriguingly, delayed DV treatment appeared to normalize the histology of the stroke affected brain such that little to no histologic dysmorphic areas indicative of infarcts could be identified, within areas consistently damaged by the stroke model, on PSD 21. As DV was administered several (four) days after infarcts form and have maximally evolved in volume in this stroke model (PSD 3)[6], the results suggest the possibility that such delayed DV administration regenerated infarcted brain tissue by promoting neurogenesis into and surrounding the stroke affected brain. This possibility is further supported by the previous observations that DV treatment after MCAo results in chronic suppression of infarct/peri-infarct astrogliosis and proteoglycan scar which would otherwise serve as a physical barrier to neuroblasts migrating towards infarcted brain tissue and extending neurites to form new synaptic connections[7]. Also of note, significant functional improvement by at least one measure (rotor rod) was observed 24 hours after the first PSD 7 administration of DV. This rapid DV-induced functional improvement is consistent with a previous study, which demonstrated a similar significant functional improvement 24 hours after the first post-stroke DV dose (given on PSD 1 in the same MCAo stroke model)[22].

Three to 14-days post-stroke has been highlighted as a critical window to start treatments, as this is when the brain is most plastic[47]. A prime example of this is an experiment where rats were exposed to enriched rehabilitation starting either 5, 14 or 30-days after MCAo, and only those animals that received early rehabilitation (5 or 14-days post-stroke) showed significant recovery[48]. Consistent with this finding, it has been shown that targeted pharmacotherapy and pharmacogenetic therapy during this early period of recovery can be of benefit. Indeed, treatments targeting activity-dependent processes (both GABAergic and glutamatergic[49-51]) 3-5 days post-stroke improve functional recovery. Similarly, targeting growth differentiation factor 10 (GDF10) 7-days post-stroke, neurite outgrowth inhibitor (NOGO) during the first 2-weeks post-stroke[52], or giving spinal delivery of chondroitinase ABC to aged 16-month old rats 3-days post-stroke[53] have all shown promise pre-clinically. While it is often difficult for monotherapies to achieve a significant effect after delayed administration, some combined therapies have also shown promise; fluoxetine combined with physiotherapy (5-10 days after stroke in humans), stem cell factor combined with granulocyte-colony stimulating factor (3.5 months after experimental stroke in rats), or AMPAKine+BDNF delivery (5-days post-stroke in 2 yr old mice) have shown some benefit[54-56]. Interestingly, delayed (1 week) fluoxetine monotherapy after stroke in rats increased post-stroke neurogenesis, but unlike DV, did not increase the survival or differentiation of neuroblasts into mature neurons or improve sensorimotor recovery[57]. Likewise, in a recent study, 7-day delayed fluoxetine monotherapy was ineffective in improving NIH stroke scale or Barthel index in ischemic stroke patients[58]. Therefore, the effectiveness of delayed DV administration in experimental stroke suggests that DV has neurogenic and therapeutic function distinct from its acute neuroprotective effects and supports a broad therapeutic window for DV stroke therapy.

Several studies have suggested that perlecan plays an important role in developmental neurogenesis. Indeed, perlecan is expressed in brain BMs and the neuroepithelial basal lamina during fetal mouse and human development[10-12] and is a major component of brain vascular BMs[9] at the interface of linked angiogenesis and neurogenesis processes[22]. Furthermore, complete perlecan deficiency results in defective fetal mouse brain neurogenesis and diminished FGF-2 driven neurogenesis[9,14,15]. Additionally, full length bovine perlecan promotes neural stem/precursor proliferation and neuritogenesis in vitro[16]. However, present inventors' studies are the first to demonstrate that perlecan could also play an important role in post-stroke neurogenesis; ninety percent perlecan-reduced mice (pln −/−) used in this study have impaired post-stroke neurogenesis but no overt developmental brain abnormalities[6], suggesting that there is enough perlecan present (or some as yet undefined compensatory mechanism) in these mice to support developmental, but not post-stroke, neurogenesis.

In agreement with the particular importance of perlecan and DV in post-stroke neurogenesis, DV is rapidly and persistently (for weeks) generated in stroked rodent brains suggesting that it is available at the proper times to impact post-stroke neurogenesis[6,8], a process that is intimately linked to angiogenesis. Likewise, it was demonstrated that DV levels, are chronically elevated in human stroke brain tissue (beyond PSD 90). While it is also important to note that the possibility of age, gender, or the cause of death of patients impacting post-stroke brain DV levels cannot be entirely ruled out in the current study, the results seemingly contradict a previous experimental stroke study that demonstrated diminished perlecan immunoreactivity rapidly (within 1 hour) and persistently (out to PSD7) in pen-infarct blood microvessels in nonhuman primates[23]. However, this study did not employ antibodies that would specifically recognize perlecan DV, but rather recognized other domains (DIV) of the perlecan protein core, implying a potentially differential expression of perlecan domains post-stroke. It is conceivable that species specific differences in DV expression exist between human and non-human primate after stroke. However, since it has been shown that DV exerts its biological activity upon cleavage from perlecan DIV by proteases such as cathepsin B/L and stromelysin/MMP3[59,60], it is tempting to hypothesize that, DV is proteolytically liberated from pre-existing perlecan in the vascular basement membrane acutely after stroke, followed by rapid degradation of DIV and other portions of perlecan, thereby explaining the diminished post-stroke DIV immunoreactivity noted by Fukuda et al[23]. Such a hypothesis would also be consistent with observations that at up to 7 days after MCAo in rats, DV pen-infarct immunoreactivity is much more abundant than DIV[6].

The acute drop in DV immunoreactivity might then be followed by a subacute and chronic increase in new perlecan and DV expression with potential to impact chronic brain responses to stroke. Indeed, a recent study has linked chronic (1-3 months) plasma increases in stromelysin/MMP3 in human stroke patients undergoing intensive rehabilitation with better functional motor recovery and to patients with greater improvements during intensive rehabilitation, independent of baseline stroke characteristics[61]. This suggests the intriguing possibility that the increased MMP3 could contribute to chronically elevated brain DV levels and better stroke outcomes with rehabilitation. Collectively, the studies support that the DV portion of perlecan, in particular, is a likely effector of developmental and reparative brain neurogenesis in both experimental and human stroke.

DV's Effects on Neocortical Excitability

Whole-cell patch-clamp recordings used as an additional approach to examine the effect of delayed DV treatment on neocortical excitability. Neocortical layer 2/3 was selected for analysis in order to determine how this prominent input layer is affected by stroke injury and by post-stroke DV treatment[26]. Increased excitatory synaptic drive to L2/3PCs was identified 21 days following transient MCAo. Rodent models of cortical dysplasia also exhibit increased excitatory synaptic drive within neocortex, thus raising the possibility that this is a common consequence of injury to this brain region[62]. Delayed DV treatment in injured animals reversed these effects and restored excitatory signaling to sham control levels. DV's restoration of excitatory drive persisted in the presence of TTX and was not paralleled by changes in EPSC amplitude or kinetics thereby suggesting a local and pre-synaptic mechanism of action at neocortical layer 2/3 synapses. These effects provide converging evidence that systemic DV treatment has robust effects on the brain and occur at a time-point that parallels the downstream neurogenic effects of DV within pen-infarct tissue.

DV Neurogenesis Effects In Vitro

To further investigate the role of DV in various stages of neurogenesis, including proliferation, migration, and differentiation, the in vitro neurosphere system was employed. While the rodent neurosphere system has been used for over 20 years[27,28], human NPCs can also undergo sphere expansion proliferation, adherent radial migration, and differentiation into βIII-Tubulin positive neurons[63], suggesting that the neurosphere system is relevant to human biology. One limitation of these in vitro neurite extension studies is that cells of fetal (commercially available) or neonatal origin were used, respectively, rather than cells derived from the adult mouse brain which might better model the in vivo stroke studies done in adult mice. This was done as neurospheres and cultured primary cortical neurons from fetal/neonatal sources confer significant advantages over adult-sourced cells toward facilitating in vitro studies (i.e. cell robustness) and there use is, therefore, widespread.

Enhanced NPC proliferation with DV was determined by four approaches. DV administration was demonstrated to increase proliferation via neurosphere expansion, viable cell numbers, MTS assays, and BrdU immunoreactivity. This result is consistent with both the in vivo observations and other studies that have demonstrated that perlecan deficiency decreases the size of the neural progenitor population in the subventricular zone in vivo and blocks FGF-2-induced formation of neurospheres in vitro[14,15], and that full-length bovine perlecan promoted neural stem/neural precursor cell proliferation in vitro[16]. The in vitro proliferation results suggest that DV alone (separated from all of perlecan) is capable of promoting a viable neuronal cell population and neurogenic niche.

To distinguish DV effects on migration of NPCs out of neurospheres, migration assays were performed with neurospheres adherent to PDL/laminin, which accelerated cell migration compared to PDL alone. This finding was in agreement with previous work showing that laminin and fibronectin substrates increased neurosphere cell migration compared to gelatin[64,65]. DV increased migration as measured by the distance that cells migrated out of the neurospheres. DV also increased NPC differentiation into neurons as indicated by increased βIII-Tubulin immunoreactivity and DCX gene expression. These findings further support the results in vivo inasmuch as DV signals new DCX+ neuroblasts to migrate from their neuronal niche and mature into new neurons (as indicated by increased BrdU and NeuN co-immunoreactivity in the stroke affected cortex).

DV Neuritogenesis Effects In Vitro

Neurite extension is an important process during brain development and neurorepair. During the latter, as previously mentioned, astrogliosis and the deposition of certain extracellular matrix proteoglycans such as neurocan and phosphacan are well-known to inhibit neurite extension, thereby ultimately limiting neurorepair[7]. Therefore, the finding that DV can support neuronal regeneration and the sprouting of new connections in scar-like conditions of stretch-induced astrogliosis in vitro is particularly significant as it suggests that delayed DV treatment could promote post-stroke brain regeneration regardless of whether it also significantly limits scar formation (as suggested in acute DV treatment stroke studies[7]). Multiple extracellular matrix components have been demonstrated to increase neurite extension in vitro including laminin, fibronectin, collagen IV, the heparan sulfate proteoglycan glypican, and full-length bovine perlecan[16,64,66,67,] and β1 integrins have frequently been implicated in these effects[31-33]. The results demonstrate that the DV portion of perlecan alone in a soluble state is sufficient to enhance neuritogenesis in vitro and are consistent with the in vivo results demonstrating that post-stroke DV administration increased pen-infarct neurite density (increased MAP2 immunofluorescence).

DV, α2β1 Integrin and Neurogenesis

In the present study, the potential mechanism(s) by which DV exerted its neurogenic effects was investigated with a particular focus on the previously determined α2β1 integrin DV receptor[6,7,43,68]. Interestingly, α2β1 integrin has been linked to neurite extension in retinal ganglion cells[34] and (31 integrin has been implicated in neurogenesis[31-35].

Collectively, the results suggest that DV may enhance post-stroke neurogenesis and improve post-stroke functional outcome via interaction with the α2β1 integrin given that: 1) α2β1 blockade prevents DV-induced post-stroke neurogenic and functional therapeutic benefits in vivo, 2) post-stroke DV treatment could not rescue impaired neurogenesis in α2β1 KO mice, 3) blockade of α2β1 integrin prevents DV's effects on NPC migration, differentiation and FCN neurite extension in vitro. This hypothesis is summarized in FIG. 8K. DV increased α2 integrin transcription by 2-4 fold in NPCs (which could also be blocked by α2 nAb), suggesting a potential positive auto-feedback loop. Furthermore, α2β1 is involved in the differentiation of these NPCs into neurons in that the blockade of α2 decreased gene expression of DCX, and DV was not able to reverse this effect in DCX expression. Importantly, cell surface integrin receptors such as α2β1 integrin function to anchor cells to extracellular matrix components such as collagen, laminin, fibronectin, etc. Therefore, in the case of proliferating neurospheres in this study which were grown as non-adherent cells in suspension in cell media, integrins are minimally expressed. Consistent with this, DV's neurosphere proliferative effects were not able to be blocked with the α2 integrin nAb (data not shown) suggesting the possibility that DV could work via additional mechanism(s) to affect neurosphere proliferation. In line with this result, post-stroke blockade of α2β1 integrin had a greater inhibitory effect on DV-driven neurogenesis on DCX positive cells in the peri-infarct region versus the periventricular region. One possibility is that this is due to the experimental design in which a2 integrin function blocking antibody was given on PSD 3, while DV treatment was initiated six hours after stroke. This could allow for DV to initiate a neurogenic effect (increase the number of DCX positive cells in the periventricular region) with subsequent migration of these cells into the peri-infarct region being blocked by the α2 integrin nAb (in agreement with the in vitro neurosphere migration results (FIG. 6D, E)). Alternatively, and perhaps more likely, DV effects on neuroblast proliferation may occur independently of and integrin. Preliminary in vitro results in the lab suggest that DV's neurosphere proliferative effects are mediated, at least in part, by the neurogenesis promoting growth factor IGF-1[69], as DV treatment appears to increase neurosphere IGF-1 levels (as measured by western blot), and can be blocked by the addition of IGF-1 nAb (data not shown). Additional experiments to delineate DV's neurogenic proliferative mechanism of action are ongoing in the laboratory.

As mentioned above, the inherent role of α2β1 integrin in post-stroke neurogenesis is also supported by the observation that neurogenesis is significantly impaired in 431 integrin KO mice and that post-stroke blockade of 431 integrin in WT mice significantly decreased the number of DCX positive periventricular cells. The present inventors are the first to report the role of α2β1 integrin in post-stroke neurogenesis. Interestingly, both stroked decoy treated control and α2 integrin nAb treated mice had very low, near identical peri-infarct DCX positive cell numbers. This, coupled with the observation that α2β1 integrin blockade alone did not further worsen functional stroke outcome below controls, could suggest that baseline neurogenesis after photothrombotic stroke may have minimal impact on functional recovery, but is susceptible to therapeutic targeting to significantly improve outcomes by treatments such as DV. Alternatively, post-stroke α2β1 integrin blockade alone could have additional, as yet unknown, effect(s) that cumulatively result in unchanged functional stroke outcome.

Conclusion

Perlecan DV increases neurogenesis and normalizes neocortical excitability in vivo after experimental stroke in young and aged mice as well as several stages of neurogenesis in vitro. This effect coincides with improved functional outcomes, even after delayed initiation of treatment, suggesting a potentially broad therapeutic window for DV. These effects may be mediated, at least in part, by α2β1 integrin, a receptor that has been demonstrated to play a key, and previously unrecognized role in post-stroke neurogenesis.

While perlecan has been implicated in developmental neurogenesis, these studies are the first to demonstrate that it is also important for post-stroke neurogenesis, and that its small DV protein portion could be used as an exogenous stroke therapy with a highly clinically relevant broad therapeutic window.

Examples 1-10: Materials and Methods

Adherence to STAIR Criteria: In an effort to increase the rigor and reproducibility of these studies, the efficacy of DV in different stroke models was tested (transient tandem ipsilateral CCA and MCA occlusion, and the permanent photothrombotic model) and different labs around the world, the Bix lab (University of Kentucky, USA) and the Clarkson lab (University of Otago, New Zealand), respectively, as suggested by the STAIR recommendations for preclinical stroke research[76]. Likewise, all studies were randomized and the experimenter(s) blinded to treatment conditions to ensure unbiased data collection and data processing. Young and aged single-sex animals were used.

Human Brain Tissue Immunohistochemistry: Postmortem brain tissues from autopsy-confirmed cases of ischemic stroke and controls were obtained from National Cerebral and Cardiovascular Center (Japan). Informed consent was secured from all subjects in this study. Experiments involving human subjects were performed in accordance with relevant guidelines and regulations and were approved by the ethics committee of National Cerebral and Cardiovascular Center. Six micrometer thick human brain sections of paraffin-embedded blocks were used for immunohistochemistry. Slides were placed at 37° C. overnight, deparaffinized in Xylene (3×5 min), and rehydrated in sequential graded alcohol to water (2×2 min at 100%, 2×2 min at 95%, 1×1 min at 80%, and 3× distilled water). To unmask the antigen, slides were heated at pH 6 (Cell Marque, Declare) for 20 min and washed in distilled water (3×5 min). Endogenous peroxidase activity was blocked in the tissue with 3% (v/v) $H_2O_2$ in methanol (Sigma), slides were rinsed in distilled water (2×2 min), PBS (2×2 min), and blocked in 10% (v/v) normal goat serum (Sigma) for 1 hr. Mouse anti-human endorepellin/Perlecan DV (1:100, R&D Systems MAB2364) was added overnight at 4° C. in a humidified chamber. Slides were washed in PBS (2×2 min), incubated with a secondary goat biotinylated anti-mouse IgG (H+L) (1:100, Vector) for 1 hr at room temperature, and washed in PBS (2×2 min). Signal was amplified using avidin-biotin substrate (Vector Laboratories) for 60 min at room temperature and developed with DAB chromogen (Dako) checking microscopically for development, and rinsed in $diH_2O$. Slides were counterstained with Harris Hematoxylin (30 second, rinsed in $diH_2O$, dipped in acid alcohol (1% HCl in absolute EtOH), rinsed in $diH_2O$, 3-5 dips in ammonia water (3 drops/100 mls $diH_2O$), and rinsed in $diH_2O$. Slides were then dehydrated in sequential water to ethanol (1×1 min at 80%, 2×2 min at 95%, and 2×2 min at 100%), cleared in Xylene and mounted. All slides were scanned on the AperioScanScope XT digital slide scanner at 40× and stitched together to create a single 1× micrograph of the tissue. Images were viewed on imagescope and infarcted regions were positively identified by a neuropathologist. Images were normalized on Adobe Photoshop to match background of control samples between multiple days of imaging. Images were further analyzed with ImageJ (NIH) to deconvolute and separate the colors for specific quantification of DAB through optical density. All images were normalized to day specific controls and observations were identified by an investigator blinded to the conditions.

Tandem Ipsilateral Common Carotid and Middle Cerebral Artery Occlusion Stroke Model: The experimental protocol was approved by the Institutional Animal Care and Use Committee of the University of Kentucky and experiments were performed in accordance with the Guide for the Care and Use of Laboratory Animals of the National Institutes of Health as well as the ARRIVE guidelines. All experiments were performed in a blinded fashion using randomized selection. Mice were housed in a climate-controlled room on a 12-hour light/dark cycle and food and water were provided ad libitum.

WT male (3 months old) C57Bl/6J, perlecan deficient (pln −/−, in a C57Bl/6J background) or α2 integrin deficient (α2 KO, in a C57Bl/6J background) mice were subjected to transient tandem ipsilateral common carotid artery (CCA)/middle cerebral artery (MCA) occlusion (MCAo) for 60 minutes as previously described (n=28)[6], followed by reperfusion of both arteries for up to 21 days. Briefly, a small burr hole was made in the skull to expose the MCA and a metal wire with a diameter of 0.005 inch was placed under the artery. Slight elevation of the metal wire causes visible occlusion of the MCA. The CCA was then isolated and occluded using an aneurysm clip. Diminished blood flow was confirmed with Laser Doppler Perfusion Monitor (Perimed) and only those animals with a diminished blood flow of at least 80% and re-establishment of at least 75% of baseline levels were included in subsequent experimentation. Animals were excluded from the study if the middle cerebral or common carotid artery was punctured during wire and clamp insertion or removal, died following surgery in recovery or were euthanized before the end of the study due to poor health. Overall, there is <5% death rate for the stroke model following surgery.

Mice were randomly assigned to a control group receiving no treatment, I.P. injections of PBS, or to a DV-treated group receiving I.P. injections of 2 mg/kg recombinant human DV, purified as described previously[6]. Injections were administered beginning on post-stroke day (PSD) 7 and every 3rd day up to PSD 19. WT mice were sacrificed on PSD 21 while pln −/−mice were sacrificed on PSD 14. Brains were extracted, flash frozen in liquid nitrogen and stored at −80° C. until further use. Brains were then sectioned (20 μm) using a cryostat (Leica) and placed on slides and stored at −20° C. until staining.

Photothrombosis Stroke Model: All procedures were carried out as per the guidelines specified by the University of Otago Animal Ethics Committee and experiments were performed in accordance with the ARRIVE guidelines. Male (24 months old) C57Bl/6J mice were subjected to focal ischemic stroke by photothrombosis as previously described (n=20)[49,50]. Briefly, Rose Bengal (200 μL of a 10 mg/mL solution; Sigma) was administered I.P. 5 min before 15 min illumination through the intact skull over the motor cortex. The area of damage affected by the stroke includes sensory forelimb and hindlimb as well as primary forelimb and hindlimb cortical areas[71]. Body temperature was maintained with a heating pad throughout the operation. Mice were randomly assigned to receive I.P. injections of DV (2 mg/kg) or PBS vehicle control beginning 6 hours after injury, then on PSD 1, 2, 4, and 6, and were sacrificed 7 days after injury by paraformaldehyde perfusion. The tissue was then post-fixed, and cryoprotected in sucrose before sectioning (10 μm).

Alternatively, young (2-3 month old) mice were randomly assigned to receive I.P. injections of DV (2 mg/kg) or PBS vehicle control (n=16 per group) beginning 6 hours after injury, then on PSD 1, 2, 4, 6, 8, 10, 12 and 14. Starting on PSD 3, the two groups of 16 mice were further divided to produce four groups of 8 and an α2-blocking antibody (1 ml of a 1 mg/ml solution; #103507, Biolegend) or IgG control antibody (1 ml of a 1 mg/ml solution; #400915, Biolegend) was injected into the brain at AP+0.00, ML−1.2, DV−2.5 (n=8 per group). The Hamilton syringe was left in place for 5 minutes post-injection to allow for proper diffusion. Functional recovery was assessed at 1 week pre and 1, 2, 4, and 6 weeks post stroke. Mice were sacrificed 6 weeks post stroke by paraformaldehyde perfusion and brain tissue was collected as described above.

Behavioral Testing: All testing was performed in a blinded fashion (tester was blind to the treatment; treatment administrator was blind to behavioral outcome). Mice (n=28) were tested on the Rotor Rod (San Diego Instruments) to examine forced motor coordination and with the Grip Strength (San Diego Instruments) test to evaluate muscle strength in the forelimbs. Behavioral testing took place prior to stroke surgery (training and baseline measurement) and on PSD 1, 4, 6, 8, 11, 13, 15, 18 and 20. The mice were placed on the Rotor Rod for 5 minutes with an increasing acceleration from 0-20 rpm for 3 trials and the parameters were set to measure distance (cm). If animals remained on the rod at the end of 5 min the test was ended and they were given a maximum distance score of 543.5 cm. For grip strength, the animals were allowed to grip a metal grid attached to a digital force-gauging apparatus and pulled until the animals let go. The amount of force (g) used was then recorded. Each animal underwent 3 trials per testing day.

Mice (n=8) were also tested with the Cylinder to evaluate spontaneous forelimb use and with the Grid Walk to assess motor impairment. Testing took place prior to surgery to establish baseline levels and then on weeks 1, 2, 4, and 6 following stroke. The mice were placed in a glass cylinder for 5 minutes and time spent using the left, right or both paws were recorded. For the grid walk, mice were allowed to walk over a metal grid and the number of foot faults and total steps taken were measured and are reported (percent of foot faults relative to total steps taken) as previously described[49,50,71].

Histology: Hematoxylin and Eosin (H&E) staining (n=13) was performed at the University of Kentucky hospital histology laboratory with the Leica Autostainer XL and Leica CV5000 Coverslipper using standard H&E methods with Harris' Hematoxylin. H&E dismorphic areas were defined as regions with loss, lower density, smaller, irregular shaped nuclei or irregular tissue patterning from surrounding areas. Areas were calculated using the ImageJ (NIH) free-hand selection tool and averaging area calculations made by the program across 3 individual tracings for each image. Regions of interest (ROI) of fixed area were selected based on the reproducible area in which stroke infarcts are generated using the MCAo experimental stroke model in mice, which were readily visible. Images were analyzed using Adobe Photoshop (threshold pixel intensity made similar across all images to isolate dark hematoxylin staining and then recorded the number of hematoxylin positive pixels).

Immunofluorescence: Tissue sections were fixed with ice cold acetone/methanol prior to incubating in blocking buffer (5% BSA in PBS with 0.1% Triton X-100) for one hour at room temperature. The sections were then incubated overnight at 4° C. in primary antibody (in 2% BSA/0.1% Triton X-100) against doublecortin (DCX, 1:1000; ab18723, Abcam) or NeuN (1:200; ab104224, Abcam). Sections were washed and incubated with a fluorescent secondary antibody (1:1000; AlexaFluor 488 or 568, Life Technologies) for one hour at room temperature. Sections were washed again and then coverslipped with fluorescent mounting media containing DAPI (H-1200, Vector Labs) and images were captured using a Nikon Eclipse Ti microscope and software (Nikon). Images were analyzed for antibody-specific positive staining using Adobe Photoshop (threshold pixel intensity made similar across all images to isolate antibody-specific staining and then recorded the number of stain positive pixels). Results are from 3 sections per animal and the area selected was in the infarct core identified morphologically.

For staining of cells, 4% paraformaldehyde was used as fixation and cells were permeabilized with 0.3% Triton X-100. Cells were blocked in 10% BSA followed by incubation with primary antibody βIII-Tubulin (1:1,250; ab18207, Abcam) overnight at 4° C. Cells were then incubated with fluorescent secondary antibody (1:250; AlexaFluor 488, Life Technologies) for 30 min at 37° C., and counterstained with DAPI as above. Images were captured as above, and differentiation was reported as the percentage of βIII-Tubulin positive cells (defined as neurons), clearly distinguishable by staining and morphology, of total DAPI positive cells.

Neurosphere Cell Culture and BrdU Incorporation and Immunofluorecence: Neurosphere-dissociated cells (isolated from E14.5 CD-1 albino mice and cryopreserved as neurospheres on day 7 of passage 1 at $5 \times 10^6$ cells in 1 mL total volume, purchased from STEMCELL Technologies (#00331)) were plated as in migration experiments on PDL. These cryopreserved neurospheres are functionally comparable to non-cyropreserved neurospheres—STEMCELL. Cells were cultured and passaged following STEMCELL Technologies Technical Manual v2.0.0 using STEMCELL reagents. Briefly, cells were maintained in T-75 cm$^2$ flasks (#658175, CellStar) at 37° C. and 5% $CO_2$, in complete proliferation media—STEMCELL Technologies NeuroCult NSC Basal Medium (#05700) with NeuroCult NSC Proliferation Supplement (#05701) and 20 ng/mL final concentration of recombinant human epidermal growth factor (rhEGF, #02633). BrdU (5-bromo-2'-deoxyuridine, #550891, BD Pharmingen) compound was administered twice daily beginning on day after plating (DAP) 1, and manufacturer instructions were followed for immunocytochemistry performed on DAP 4, 30 min after the final BrdU administration. Results are from 4 independent experiments with conditions performed in duplicate and at least 2 images taken per well.

In addition, mice were injected with BrdU 100 µl of 10 mg/kg) following MCAo on PSD 7-13 and again on PSD 20-21 to visualize new cells within the brain. Immunofluorescence for BrdU was performed following the manufacturer's protocol (Abcam). Brain sections were fixed with 4% paraformaldehyde for two hours at room temperature. They were then washed in PBS with 1% Triton X-100 and incubated in 1N HCL for 10 mins on ice to break open the DNA structure of the BrdU-labelled cells, and this was followed by 2N HCl for 10 minutes at room temperature before moving them to an incubator for 20 mins at 37° C. After the acid washes, 0.1 M borate buffer was added for 12 mins at room temperature. Brain slices were washed again in PBS-1% Triton X-100 and blocked (5% BSA with 1% Triton X-100). Sections were incubated for 2 nights at 4° C. in primary antibody against BrdU (1:200; ab6326, Abcam) and then fluorescent secondary antibody (1:2000; AlexaFluor 568) for 1 hour at 37° C. Sections were coverslipped with mounting media containing DAPI and images were taken as described above.

Neocortical Slice Preparation: All methods, as well as contents of artificial cerebrospinal fluid (ACSF) and internal pipette solutions have been reported previously unless otherwise stater[72,73]. On the 21$^{st}$ day following sham-injury or ischemic injury using MCAo, mice were decapitated while anesthetized by isoflurane inhalation. Neocortical slices (350 µM) slices were cut in the coronal plane. Each dorsal half of the hemisphere located ipsilateral to injury or sham injury was then isolated and stored in a holding chamber containing ACSF.

Electrophysiology: After equilibration (>1 hour), slices were transferred to a recording chamber on an upright, fixed-stage microscope equipped with infrared, differential interference contrast optics (IR-DIC; Olympus BX51WI), where they were continually superfused with warmed (32-34° C.) ACSF. Whole-cell patch-clamp recordings were performed from visualized neocortical layer 2/3 pyramidal cells; the investigator was blinded to animal treatment. Cells were targeted in agranular cortex. Cell selection began at the boundary to granular cortex, using layer 4 as a visual landmark, and continued in the medial direction. Recording pipettes from borosilicate glass capillaries were filled with 130 mM K$^+$-gluconate[72]. Neural activity was recorded using an Axon Multiclamp 700B patch-clamp amplifier (Molecular Devices), acquired at 10-20 kHz and low-pass filtered at 5 kHz using a Digidata 1440A digitizer and pClamp software (v10.3; Molecular Devices). Open tip resistance was 2-5 MΩ, seal resistance was 1-5 GΩ, series resistance was uncompensated and was required be <25 MΩ with <20% change during the recording (mean=15.07±0.65 MΩ, n=34). Reported membrane potential values were not adjusted for liquid junction potential of −7 mV.

Cells were allowed to acclimate >5 minutes following establishment of whole-cell configuration. Intrinsic properties were measured first. Membrane potential was recorded in 1=0 mode and analyzed in a 15-second interval. Input resistance was measured as the slope of the linear component of steady-state voltage responses to a series of current steps (−40 pA steps of 500 msec; range+160 to −200 pA) using pClamp. Action potential thresholds were tested with minimum depolarizing current steps (+50 pA steps of 500 msec) and analyzed using Minianalysis (6.0.3; Synaptosoft).

The type A GABA receptor antagonist bicuculline methiodide (30 µM; Tocris Bioscience) was then added to the bath in order to isolate for sEPSCs. Tetrodotoxin (1 µM; Alomone Labs) was added to the bath in order to examine mEPSCs. sEPSCs and mEPSCs were recorded in voltage-clamp mode with a voltage command of −65 mV. Synaptic currents were analyzed off-line on a PC-style computer with Minianalysis. The detection limit for synaptic currents was 3× the root mean squared noise level for each recording. A single-exponential EPSC decay time constant was measured in Minianalysis using a Fraction of Peak to Find a Decay Time setting of 0.37 with no weighted adjustments. All electrophysiological parameters were averaged across neurons (i.e., n=number of neurons).

At the conclusion of each cell recording, 3 sets of X and Y coordinates were collected by placing the patch pipette tip in 3 locations and recording the values provided by a micromanipulator control unit (ROE-200; Sutter). These three sets of X and Y coordinates included the location of the recorded neuron, the location of the most dorsal-medial aspect of the tissue slice and the location of the most dorsal aspect of the macroscopic lesion, along the cortical surface, in injured animals. These sets of coordinates were used to calculate X and Y distances between the recorded cell and each of these other two landmarks. For each X-Y pair, the hypotenuse (square root of the sum of squared X and Y values) was then obtained to generate a single straight-line distance from the location of the recorded neuron to each of these two landmarks.

QCR: Experiments were terminated at HAP 6 for migration experiments and on DAP 3 for differentiation experiments. The cells were quickly washed and preserved in Trizol Reagent (#15596026, Life Technologies), RNA was extracted from cells using the PureLink™ RNA Mini Kit (#1283018A, Life Technologies), and converted into cDNA using the High-Capacity cDNA Reverse Transcription Kit (#4368814, Applied Biosystems) using manufacturers' instructions. Real-time PCR was performed with TaqMan fast advanced master mix (#4444557, Applied Biosystems), with normalization to the housekeeping gene 18s, using the ViiA™ 7 qPCR system (Applied Biosystems). n=3; cells pooled from duplicate wells per condition per experiment. Fold changes were determined using the ΔCt method[74].

Neurosphere Expansion Assay: At the time of neurosphere passaging, dissociated cells were plated in 24-well plates at 2×10$^4$ cells/well in 1 mL volume of complete proliferation media or conditions as defined. Recombinant human DV was used at 300 nM in all experiments. Pictures were taken daily to monitor neurosphere growth and expansion under phase-contrast microscopy with a VWR VistaVision microscope and a Moticam 2.0 MP camera (Motic) using Motic Images Plus 2.0 software for Macintosh OSX (used for all non-fluorescent imaging). Images were analyzed using ImageJ software (NIH), following a pixels-to-µm calibration, to measure the neurosphere diameter, which was calculated as the average of the longest vertical axis and longest horizontal axis. Viable cell counts of each condition were obtained by trypan blue exclusion at the end of each experiment. Conditions were performed in duplicate with at least 3 images taken per well per day, over 200 neurospheres quantified per condition per DAP, from 3 independent experiments.

Neurosphere Proliferation Assay: At the time of neurosphere passaging, dissociated cells were plated in 96-well plates at 2,500 cells/well in 250 µL volume of complete proliferation media or conditions as defined. Formazan dye (MTS)-based assays were performed 48 HAP neurosphere-dissociated cells, following the Promega Non-Radioactive Cell Proliferation Assay Technical Manual, by incubating 50 μL MTS/PMS solution per well for 2.5 hr before reading absorbance on a plate reader at 490 nm.

Neurosphere Migration Assay: Migration assays were performed in 24-well plates coated either with 100 μg/mL Poly-d-Lysine (PDL; #P6407, Sigma) or PDL followed by mouse laminin (15 μg/mL; #23017-015, Life Technologies). Immediately prior to passaging, isolated whole neurospheres were plated at a very low density (~1,600 cells/well) in proliferation media with no EGF. Brightfield images (non-phase contrast) were captured at 0, 4, 12, and 24 HAP on PDL, and at 30 min and 6 HAP on PDL/laminin. Upon passaging, whole neurospheres were allowed to adhere for 30 minutes prior to α2 nAb treatment and then were allowed to incubate for 15 minutes prior to DV or Vehicle treatment. PDL experiment results were from 4 independent experiments, with each condition performed in duplicate, and the same 3 cell clusters monitored per well. Cell cluster diameter (μm, where normalized cluster diameter=diameter at each time point divided by its own diameter at the 0 time point) was measured using ImageJ software (NIH). PDL/laminin results were from 5 experiments, with each condition performed in duplicate, and the same 3 neurospheres monitored per well, from which the 10 farthest travelling cells at 6 hr were quantified. Migration distance (μm), =Distance from cell leading edge to center of neurosphere (6 h)−radius of the original neurosphere (30 min)/diameter of the original neurosphere (30 min), was measured using ImageJ software. The radius and diameter factors were included in the migration distance equation to account for the cell's migration point of origin and normalization for the size of the originating neurosphere, respectively.

Neurosphere Differentiation: Differentiation assays were performed in 24-well plates coated with 100 μg/mL PDL followed by 15 μg/mL mouse laminin and used on the day of coating. At the time of passaging, single cells were plated at 2.5×10$^5$ cells/well in 1 mL volume of differentiation media or conditions as defined and were allowed to adhere for 30 minutes prior to α2 nAb treatment and then were allowed to incubate for 15 minutes prior to DV or Vehicle treatment. Differentiation media consisted of STEMCELL Technologies NeuroCult NSC Basal Medium (#05700) with NeuroCult NSC Differentiation Supplement (#05703). Cells remained in culture in differentiating conditions until immunocytochemical analysis on DAP 6. Results were from 4 independent experiments, with conditions performed in duplicate or triplicate, with 3 images taken per well.

Neurite Extension Assays: E16 C57Bl/6J mice fetal cortices, yielding >90% of neurons, were isolated as described previously[75]. The neurons were then plated in 96-well plates coated with PDL (50 μg/mL) at 100,000 cells/well in 100 μl/well of the DMEM/B27 media (Gibco) and incubated overnight at 37° C. Treatment conditions were then applied to the cells without B27 supplement. After 4 hours in treatment media, neurons were fixed with 4% paraformaldehyde for 30 min at 4° C. and stained with 0.1% cresyl violet solution for 30 min. Images were captured using the VWR microscope above and analyzed using NeuronJ and Simple Neurite Tracer plugins for Image J software (NIH) and reported as number of neurites, percentage of cells with at least one neurite, and number of cell-cell connections. Only neurites equal to or longer than the originating cell body diameter were counted. Results were from 5 total experiments (independent neuronal preparations), with conditions performed in triplicate per experiment, and at least 5 images analyzed per condition.

Astrocyte/Neuron Co-culture Injury Model: Cortical astrocytes were isolated from newborn mice (P1-3) as previously described[39-41]. Briefly, cells were dissociated in D-MEM/F12, supplemented with Glutamax (Gibco), 1% Pen/Strep, 10% FBS and plated in T-75 mm$^2$ flasks. After 10-12 days in culture cells were shaken for 24-36 hours and treated with 10 mM leucin methylester for 12 hours to remove oligodendrocyte precursors and microglia. Astrocyte cultures were then seeded (400,000 cells) onto deformable membrane wells (Bioflex 6 well plates, Flexcell International) coated with collagen I. After 1 week in culture the FBS in the medium was reduced to 5%, and after a further 1-2 weeks FBS was reduced to 0.5% for 48 hours and then subsequently 0% for 6 hours. Cells were then mechanically traumatized using an abrupt pressure pulse with a pneumatic device (Flexcell FX-4000 Strain Unit, Flexcell International) programmed to produce a maximal elongation of 23% (130 ms, triangular stretch). Pressure-stretched astrocytes become highly reactive within 24 hours and up-regulate axon growth inhibitors without initiating significant cell death (2% measured by propidium iodine permeability at 48 hours post-stretching). After 24 hours, cortical neurons were isolated from P5-6 mice as previously described[39,41]. Treatment with either DV or PBS was performed 6 hours after the astrocytes had been stretched. Twenty-four hours post-plating of neurons, cultures were fixed with 4% paraformaldehyde and processed for immunocytochemistry. To visualize the neurons and astrocytes a mouse TuJ1 (1:2000; #MAB1195, R&D Systems) and chicken GFAP (1:5000; AB5541, Millipore) primary antibodies respectively were used, followed by 488 and 549 DyLight dyes conjugated to affinity-purified secondary antibodies (1:1000; 715-485-150 and #703-505-155, Jackson ImmunoResearch). All cultures were counter-stained with DAPI to visualize the presence of all cells. To analyze neurite outgrowth, TuJ1-positive cells were digitized using a 20× objective (Olympus BX51 microscope). Neurite outgrowth was quantified using Image J software (NIH) and measuring the total length of all branches. For each well an area of 110 mm$^2$ was analyzed. The analysis was performed in three independent co-cultures each performed in triplicate (60-65 neurons total per condition were analyzed).

Statistics: All measured variables are presented as mean±SEM from a minimum of three independent experiments. A power analysis was conducted to ensure adequate subject numbers as detailed in the figure legends for each study. Analysis of results for comparison between two groups was performed using a Student's t-test. For comparisons across multiple groups, a One-way ANOVA followed by Tukey's post-hoc test or a Two-Way Repeated Measures ANOVA followed by Bonferroni's or Tukey's post-hoc test was used. Statistical analyses were performed with GraphPad Prism software (GraphPad Inc., CA, USA). A p value of <0.05 is considered significant.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference

REFERENCES

1. Roger, V. L., et al. Heart disease and stroke statistics—2012 update: a report from the American Heart Association. *Circulation* 125, e2-e220 (2012).
2. Maiser, S., et al. Intravenous recombinant tissue plasminogen activator administered after 3 h following onset of ischaemic stroke: a metaanalysis. *Int J Stroke* 6, 25-32 (2011).
3. Hassan, A. E., Chaudhry, S. A., Grigoryan, M., Tekle, W. G. & Qureshi, A. I. National trends in utilization and outcomes of endovascular treatment of acute ischemic stroke patients in the mechanical thrombectomy era. *Stroke; a journal of cerebral circulation* 43, 3012-3017 (2012).
4. Lees, K. R., et al. Glycine antagonist (gavestinel) in neuroprotection (GAIN International) in patients with acute stroke: a randomised controlled trial. GAIN International Investigators. *Lancet* 355, 1949-1954 (2000).
5. Investigators, E.A.S.T. Use of anti-ICAM-1 therapy in ischemic stroke: results of the Enlimomab Acute Stroke Trial. *Neurology* 57, 1428-1434 (2001).
6. Lee, B., et al. Perlecan domain V is neuroprotective and proangiogenic following ischemic stroke in rodents. *J Clin Invest* 121, 3005-3023 (2011).
7. Al-Ahmad, A. J., Lee, B., Saini, M. & Bix, G. J. Perlecan domain V modulates astrogliosis in vitro and after focal cerebral ischemia through multiple receptors and increased nerve growth factor release. *Glia* 59, 1822-1840 (2011).
8. Bix, G., Gowling, E. & Clarkson, A. Perlecan domain V is neuroprotective and affords functional improvement in a photothromotic stroke model in young and aged mice. *Transl Stroke Res* 4, 515-523 (2013).
9. Roberts, J., Kahle, M. P. & Bix, G. J. Perlecan and the blood-brain barrier: beneficial proteolysis? *Frontiers in pharmacology* 3, 155 (2012).
10. Roediger, M., Kruegel, J., Miosge, N. & Gersdorff, N. Tissue distribution of perlecan domains III and V during embryonic and fetal human development. *Histology and histopathology* 24, 859-868 (2009).
11. Gustafsson, E., Almonte-Becerril, M., Bloch, W. & Costell, M. Perlecan maintains microvessel integrity in vivo and modulates their formation in vitro. *PLoS One* 8, e53715 (2013).
12. Soulintzi, N. & Zagris, N. Spatial and temporal expression of perlecan in the early chick embryo. *Cells, tissues, organs* 186, 243-256 (2007).
13. Timpl, R. & Aumailley, M. Biochemistry of basement membranes. *Adv Nephrol Necker Hosp* 18, 59-76 (1989).
14. Giros, A., Morante, J., Gil-Sanz, C., Fairen, A. & Costell, M. Perlecan controls neurogenesis in the developing telencephalon. *BMC Dev Biol* 7, 29 (2007).
15. Kerever, A., et al. Perlecan is required for FGF-2 signaling in the neural stem cell niche. *Stem cell research* 12, 492-505 (2014).
16. Nakamura, R., Nakamura, F. & Fukunaga, S. Diverse functions of perlecan in central nervous system cells in vitro. *Animal Science Journal* 86, 904-911 (2015).
17. Arvidsson, A., Collin, T., Kirik, D., Kokaia, Z. & Lindvail, 0. Neuronal replacement from endogenous precursors in the adult brain after stroke. *Nat Med* 8, 963-970 (2002).
18. Lichtenwalner, R. & Parent, J. Adult neurogenesis and the ischemic forebrain. *J Cereb Blood Flow Metab* 26, 1-20 (2006).
19. Massouh, M. & Saghatelyan, A. De-routing neuronal precursors in the adult brain to sites of injury: role of the vasculature. *Neuropharmacology* 58, 877-883 (2010).
20. Thored, P., et al. Long-term neuroblast migration along blood vessels in an area with transient angiogenesis and increased vascularization after stroke. *Stroke; a journal of cerebral circulation* 38, 3032-3039 (2007).
21. Wang, Y., et al. VEGF-overexpressing transgenic mice show enhanced post-ischemic neurogenesis and neuromigration. *Journal of neuroscience research* 85, 740-747 (2007).
22. Ohab, J. J. & Carmichael, S. T. Poststroke neurogenesis: emerging principles of migration and localization of immature neurons. *The Neuroscientist: a review journal bringing neurobiology, neurology and psychiatry* 14, 369-380 (2008).
23. Fukuda, S., et al. Focal cerebral ischemia induces active proteases that degrade microvascular matrix. *Stroke; a journal of cerebral circulation* 35, 998-1004 (2004).
24. Kahle, M. P. & Bix, G. J. Neuronal restoration following ischemic stroke: influences, barriers, and therapeutic potential. *Neurorehabilitation and neural repair* 27, 469-478 (2013).
25. Couillard-Despres, S., et al. Doublecortin expression levels in adult brain reflect neurogenesis. *The European journal of neuroscience* 21, 1-14 (2005).
26. Hooks, B., et al. *Organization of Cortical and Thalamic Input to Pyramidal Neurons in* Mouse Motor Cortex. *The Journal of neuroscience: The Official Journal of the Society for Neuroscience* 33, 748-760 (2013).

27. Reynolds, B. A., Tetzlaff, W. & Weiss, S. A multipotent EGF-responsive striatal embryonic progenitor cell produces neurons and astrocytes. *The Journal of Neuroscience: the official journal of the Society for Neuroscience* 12, 4565-4574 (1992).
28. Reynolds, B. A. & Weiss, S. Generation of neurons and astrocytes from isolated cells of the adult mammalian central nervous system. *Science* 255, 1707-1710 (1992).
29. Parham, C., et al. Perlecan Domain V Inhibits Amyloid-B Activation of the a2b1 Integrin-Mediated Neurotoxic Signaling Cascade. *J Alzheimers Disease* 54, 1629-1647 (2016).
30. Wright, S., et al. Perlecan domain V inhibits α2 integrin-mediated amyloid-B neurotoxicity. *Neurobiology of aging* 33, 1379-1388 (2010).
31. Tisay, K. T. & Key, B. The extracellular matrix modulates olfactory neurite outgrowth on ensheathing cells. *The Journal of Neuroscience: the official journal of the Society for Neuroscience* 19, 9890-9899 (1999).
32. Mruthyunjaya, S., Rumma, M., Ravibhushan, G., Anjali, S. & Padma, S. c-Jun/AP-1 transcription factor regulates laminin-1-induced neurite outgrowth in human bone marrow mesenchymal stem cells: role of multiple signaling pathways. *FEBS letters* 585, 1915-1922 (2011).
33. Gupton, S. L. & Gertler, F. B. Integrin signaling switches the cytoskeletal and exocytic machinery that drives neuritogenesis. *Developmental cell* 18, 725-736 (2010).
34. Bradshaw, A. D., et al. Integrin alpha 2 beta 1 mediates interactions between developing embryonic retinal cells and collagen. *Development* 121, 3593-3602 (1995).
35. Leone, D. P., et al. Regulation of neural progenitor proliferation and survival by beta1 integrins. *Journal of cell science* 118, 2589-2599 (2005).
36. Durbec, P., Franceschini, I., Lazarini, F. & Dubois-Dalcq, M. In vitro migration assays of neural stem cells. *Methods Mol Biol* 438, 213-225 (2008).
37. Kouroupi, G., et al. Lentivirus-mediated expression of insulin-like growth factor-I promotes neural stem/precursor cell proliferation and enhances their potential to generate neurons. *Journal of neurochemistry* 115, 460-474 (2010).
38. Anderson, M. F., Aberg, M. A., Nilsson, M. & Eriksson, P. S. Insulin-like growth factor-I and neurogenesis in the adult mammalian brain. *Brain research. Developmental brain research* 134, 115-122 (2002).
39. Overman, J. J., et al. A role for ephrin-A5 in axonal sprouting, recovery, and activity-dependent plasticity after stroke. *Proceedings of the National Academy of Sciences of the United States of America* 109, E2230-2239 (2012).
40. Wanner, I. B., et al. A new in vitro model of the glial scar inhibits axon growth. *Glia* 56, 1691-1709 (2008).
41. Berretta, A., Gowing, E. K., Jasoni, C. L. & Clarkson, A. N. Sonic hedgehog stimulates neurite outgrowth in a mechanical stretch model of reactive-astrogliosis. *Scientific reports* 6, 21896 (2016).
42. Chen, J., Diacovo, T. G., Grenache, D. G., Santoro, S. A. & Zutter, M. M. The alpha(2) integrin subunit-deficient mouse: a multifaceted phenotype including defects of branching morphogenesis and hemostasis. *The American journal of pathology* 161, 337-344 (2002).
43. Clarke, D. N., et al. Perlecan Domain V induces VEGf secretion in brain endothelial cells through integrin alpha5beta1 and ERK-dependent signaling pathways. *PLoS One* 7, e45257 (2012).
44. Truelsen, T., et al. Stroke incidence and prevalence in Europe: a review of available data. *European journal of neurology: the official journal of the European Federation of Neurological Societies* 13, 581-598 (2006).
45. Kelly-Hayes, M., et al. The influence of gender and age on disability following ischemic stroke: the Framingham study. *Journal of stroke and cerebrovascular diseases: the official journal of National Stroke Association* 12, 119-126 (2003).
46. Gao, P., et al. Attenuation of brain response to vascular endothelial growth factor-mediated angiogenesis and neurogenesis in aged mice. *Stroke; a journal of cerebral circulation* 40, 3596-3600 (2009).
47. Murphy, T. H. & Corbett, D. Plasticity during stroke recovery: from synapse to behaviour. *Nature reviews. Neuroscience* 10, 861-872 (2009).
48. Biernaskie, J., Chemenko, G. & Corbett, D. Efficacy of rehabilitative experience declines with time after focal ischemic brain injury. *The Journal of neuroscience: the official journal of the Society for Neuroscience* 24, 1245-1254 (2004).
49. Clarkson, A. N., Huang, B. S., Macisaac, S. E., Mody, I. & Carmichael, S. T. Reducing excessive GABA-mediated tonic inhibition promotes functional recovery after stroke. *Nature* 468, 305-309 (2010).
50. Clarkson, A. N., et al. AMPA receptor-induced local brain-derived neurotrophic factor signaling mediates motor recovery after stroke. *The Journal of neuroscience: the official journal of the Society for Neuroscience* 31, 3766-3775 (2011).
51. Hiu, T., et al. Enhanced phasic GABA inhibition during the repair phase of stroke: a novel therapeutic target. *Brain: a journal of neurology* 139, 468-480 (2016).
52. Wahl, A. S., et al. Neuronal repair. Asynchronous therapy restores motor control by rewiring of the rat corticospinal tract after stroke. *Science* 344, 1250-1255 (2014).
53. Soleman, S., Yip, P. K., Duricki, D. A. & Moon, L. D. Delayed treatment with chondroitinase ABC promotes sensorimotor recovery and plasticity after stroke in aged rats. *Brain: a journal of neurology* 135, 1210-1223 (2012).
54. Chollet, F., et al. Fluoxetine for motor recovery after acute ischaemic stroke (FLAME): a randomised placebo-controlled trial. *The Lancet. Neurology* 10, 123-130 (2011).
55. Clarkson, A. N., Parker, K., Nilsson, M., Walker, F. R. & Gowing, E. K. Combined ampakine and BDNF treatments enhance poststroke functional recovery in aged mice via AKT-CREB signaling. *J Cereb Blood Flow Metab* 35, 1272-1279 (2015).
56. Zhao, J. P. & Constantine-Paton, M. NR2A−/− mice lack long-term potentiation but retain NMDA receptor and L-type Ca2+ channel-dependent long-term depression in the juvenile superior colliculus. *The Journal of neuroscience: the official journal of the Society for Neuroscience* 27, 13649-13654 (2007).
57. Sun, X., et al. Fluoxetine enhanced neurogenesis is not translated to functional outcome in stroke rats. *Neuroscience letters* 603, 31-36 (2015).
58. Guo, Y., et al. Effect of using fluoxetine at different time windows on neurological functional prognosis after ischemic stroke. *Restorative neurology and neuroscience* 34, 177-187 (2016).
59. Saini, M. G. & Bix, G. J. Oxygen-glucose deprivation (OGD) and interleukin-1 (IL-1) differentially modulate cathepsin B/L mediated generation of neuroprotective perlecan LG3 by neurons. *Brain research* 1438, 65-74 (2012).

60. Farach-Carson, M. C. & Carson, D. D. Perlecan—a multifunctional extracellular proteoglycan scaffold. *Glycobiology* 17, 897-905 (2007).
61. Ma, F. M., et al. Plasma Matrix Metalloproteinases in Patients with Stroke During Intensive Rehabilitation Therapy. *Arch Phys Med Rehabil* 97, 1832-1840 (2016).
62. Brill, J. & Huguenard, J. R. Enhanced infragranular and supragranular synaptic input onto layer 5 pyramidal neurons in a rat model of cortical dysplasia. *Cereb Cortex* 20, 2926-2938 (2010).
63. Moors, M., et al. Human neurospheres as three-dimensional cellular systems for developmental neurotoxicity testing. *Environmental health perspectives* 117, 1131-1138 (2009).
64. Andressen, C., Adrian, S., Fassler, R., Arnhold, S. & Addicks, K. The contribution of beta1 integrins to neuronal migration and differentiation depends on extracellular matrix molecules. *European journal of cell biology* 84, 973-982 (2005).
65. Kearns, S. M., Laywell, E. D., Kukekov, V. K. & Steindler, D. A. Extracellular matrix effects on neurosphere cell motility. *Experimental neurology* 182, 240-244 (2003).
66. Coles, C. H., et al. Proteoglycan-specific molecular switch for RPTPsigma clustering and neuronal extension. *Science* 332, 484-488 (2011).
67. Hill, J. J., Jin, K., Mao, X. O., Xie, L. & Greenberg, D. A. Intracerebral chondroitinase ABC and heparan sulfate proteoglycan glypican improve outcome from chronic stroke in rats. *Proceedings of the National Academy of Sciences of the United States of America* 109, 9155-9160 (2012).
68. Bix, G. & Iozzo, R. V. Matrix revolutions: "tails" of basement-membrane components with angiostatic functions. *Trends in cell biology* 15, 52-60 (2005).
69. Huat T. J., Khan A. A., Pati S., Mustafa Z., Abdullah J. M., Jaafar H. IGF-1 enhances cell proliferation and survival during early differentiation of mesenchymal stem cells to neural progenitor-like cells. *BMC Neurosci* 15:91-104 (2014).
70. Blumbach, K., et al. Dwarfism in mice lacking collagen-binding integrins alpha2beta1 and alpha11beta1 is caused by severely diminished IGF-1 levels. *The Journal of biological chemistry* 287, 6431-6440 (2012).
71. Clarkson, A. N., et al. Multimodal examination of structural and functional remapping in the mouse photothrombotic stroke model. *J Cereb Blood Flow Metab* 33, 716-723 (2013).
72. Butler, C., Boychuk, J. & Smith, B. Effects of Rapamycin Treatment on Neurogenesis and Synaptic Reorganization in the Dentate Gyms after Controlled Cortical Impact Injury in Mice. *Front Syst Neurosci* 9(2015).
73. Boychuk, J., et al. HCN channels segregate stimulation-evoked movement responses in neocortex and allow for coordinated forelimb movements in rodents. *J Physiol* 595, 247-263 (2017).
74. Livak, K. J. & Schmittgen, T. D. Analysis of relative gene expression data using real-time quantitative PCR and the 2(-Delta Delta C(T)) Method. *Methods* 25, 402-408 (2001).
75. Wright, S., et al. Alpha2beta1 and alphaVbeta1 integrin signaling pathways mediate amyloid-beta-induced neurotoxicity. *Neurobiology of aging* 28, 226-237 (2007).
76. Albers, G. W. et al. Stroke Therapy Academic Industry Recommendations for standards regarding preclinical neuroprotective and restorative drug development. *Stroke* 30, 2752-8 (1999).

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A method of enhancing recovery after an ischemic event in a subject, comprising: administering to a subject in need of neurorepair following the ischemic event an effective amount of Perlecan Domain V (DV), wherein DV is first administered to the subject more than 24 hours after the ischemic event to increase neurogenesis, and wherein administration of DV increases the number of new post-ischemic event mature neurons in an area of the brain of the subject damaged by the ischemic event.

2. The method of claim 1, wherein administering DV increases neuron survival, improves functional recovery, improves motor function, increases outgrowth of new neurons, restores excitatory synaptic transmission, reverses ischemic induced changes to excitatory post synaptic currents, increases neurosphere expansion, and/or increases neuroblast migration compared to a control subject that does not receive DV.

3. The method of claim 1, wherein the DV is first administered at least 7 days after the ischemic event.

4. The method of claim 1, wherein the ischemic event is a photothrombic stroke or a transient middle cerebral artery occlusion stroke.

5. The method of claim 1, wherein the administering step includes administering about 0.5 mg/kg to about 20 mg/kg of the DV.

6. The method of claim 1, wherein neural precursor cells and/or peri-infarct neurite density is increased.

7. The method of claim 1, wherein the administering the DV includes administering the DV intravenously or administering the DV intraperitoneally.

8. The method of claim 1 wherein the subject is a mammal.

9. The method of claim 1 wherein the administering occurs daily for a period of 2 days to two weeks.

* * * * *